(12) United States Patent
Bowen et al.

(10) Patent No.: US 10,231,484 B2
(45) Date of Patent: **\*Mar. 19, 2019**

(54) AEROSOL DEVICES AND METHODS FOR INHALING A SUBSTANCE AND USES THEREOF

(71) Applicant: Juul Labs, Inc., San Francisco, CA (US)

(72) Inventors: Adam Bowen, San Francisco, CA (US); James Monsees, San Francisco, CA (US)

(73) Assignee: Juul Labs, Inc., San Francisco, CA (US)

( * ) Notice: Subject to any disclaimer, the term of this patent is extended or adjusted under 35 U.S.C. 154(b) by 703 days.

This patent is subject to a terminal disclaimer.

(21) Appl. No.: 14/625,042

(22) Filed: Feb. 18, 2015

(65) Prior Publication Data

US 2015/0157056 A1 Jun. 11, 2015

Related U.S. Application Data

(63) Continuation of application No. 12/336,439, filed on Dec. 16, 2008, now Pat. No. 8,991,402.

(Continued)

(51) Int. Cl.
*A24F 1/32* (2006.01)
*A24F 47/00* (2006.01)
(Continued)

(52) U.S. Cl.
CPC ............. *A24F 47/008* (2013.01); *A24D 1/14* (2013.01); *A24F 47/004* (2013.01);
(Continued)

(58) Field of Classification Search
CPC .................................................. A24F 47/008
See application file for complete search history.

(56) References Cited

U.S. PATENT DOCUMENTS

| 374,584 A | 12/1887 | Cook |
| 576,653 A | 2/1897 | Bowlby |

(Continued)

FOREIGN PATENT DOCUMENTS

| CA | 2641869 A1 | 5/2010 |
| CN | 85106876 A | 9/1986 |

(Continued)

OTHER PUBLICATIONS

Grotenhermen et al.; Developing science-based per se limits for driving under the influence of cannabis (DUIC): findings and recommendations by an expert panel; retrieved Feb. 9, 2017 from (http://www.canorml.org/healthfacts/DUICreport.2005.pdf); 49 pages; Sep. 2005.

(Continued)

*Primary Examiner* — Michael H. Wilson
*Assistant Examiner* — Dionne W. Mayes
(74) *Attorney, Agent, or Firm* — Mintz, Levin, Cohn, Ferris, Glovsky and Popeo, P.C.

(57) ABSTRACT

Devices, cartridges, and method are described herein for emulating smoking wherein a device generates an aerosol for inhalation by a subject by heating a viscous material that can have a tactile response in the mouth or respiratory tract, while reducing Hoffman analytes and mutagenic compounds delivered to the user as compared to a common tobacco cigarette.

25 Claims, 16 Drawing Sheets

Related U.S. Application Data

(60) Provisional application No. 61/014,690, filed on Dec. 18, 2007.

(51) Int. Cl.

| | | |
|---|---|---|
| *A61M 11/04* | (2006.01) | |
| *A61M 15/00* | (2006.01) | |
| *A61M 15/06* | (2006.01) | |
| *A24D 1/14* | (2006.01) | |
| *B32B 7/12* | (2006.01) | |
| *B32B 15/09* | (2006.01) | |
| *B32B 27/08* | (2006.01) | |
| *B32B 27/36* | (2006.01) | |

(52) U.S. Cl.
CPC ......... *A61M 11/041* (2013.01); *A61M 11/047* (2014.02); *A61M 11/048* (2014.02); *A61M 15/0021* (2014.02); *A61M 15/0028* (2013.01); *A61M 15/0035* (2014.02); *A61M 15/0041* (2014.02); *A61M 15/06* (2013.01); *B32B 7/12* (2013.01); *B32B 15/09* (2013.01); *B32B 27/08* (2013.01); *B32B 27/36* (2013.01); *A61M 11/042* (2014.02); *A61M 2205/0266* (2013.01); *A61M 2205/125* (2013.01); *A61M 2205/3653* (2013.01); *A61M 2205/584* (2013.01); *A61M 2205/8206* (2013.01); *B32B 2255/10* (2013.01); *B32B 2255/205* (2013.01); *B32B 2307/31* (2013.01); *B32B 2307/702* (2013.01); *B32B 2307/7244* (2013.01); *B32B 2307/7246* (2013.01); *B32B 2435/02* (2013.01)

(56) References Cited

U.S. PATENT DOCUMENTS

| | | |
|---|---|---|
| 595,070 A | 12/1897 | Oldenbusch |
| 720,007 A | 2/1903 | Dexter |
| 799,844 A | 9/1905 | Fuller |
| 968,160 A | 8/1910 | Johnson |
| 969,076 A | 8/1910 | Pender |
| 1,067,531 A | 7/1913 | MacGregor |
| 1,163,183 A | 12/1915 | Stoll |
| 1,299,162 A | 4/1919 | Fisher |
| 1,505,748 A | 8/1924 | Louis |
| 1,552,877 A | 9/1925 | Phillipps et al. |
| 1,632,335 A | 6/1927 | Hiering |
| 1,706,244 A | 3/1929 | Louis |
| 1,845,340 A | 2/1932 | Ritz |
| 1,972,118 A | 9/1934 | McDill |
| 1,998,683 A | 4/1935 | Montgomery |
| 2,031,363 A | 2/1936 | Elof |
| 2,039,559 A | 5/1936 | Segal |
| 2,104,266 A | 1/1938 | McCormick |
| 2,159,698 A | 5/1939 | Harris et al. |
| 2,177,636 A | 10/1939 | Coffelt et al. |
| 2,195,260 A | 3/1940 | Rasener |
| 2,231,909 A | 2/1941 | Hempel |
| 2,327,120 A | 8/1943 | McCoon |
| 2,460,427 A | 2/1949 | Musselman et al. |
| 2,483,304 A | 9/1949 | Rudolf |
| 2,502,561 A | 4/1950 | Ludwig |
| 2,765,949 A | 10/1956 | Swan |
| 2,830,597 A | 4/1958 | Kummli |
| 2,860,638 A | 11/1958 | Bartolomeo |
| 2,897,958 A | 8/1959 | Tarleton et al. |
| 2,935,987 A | 5/1960 | Ackerbauer |
| 3,146,937 A | 9/1964 | Joseph |
| 3,258,015 A | 5/1966 | Ellis et al. |
| 3,271,719 A | 9/1966 | Ovshinsky |
| 3,292,634 A | 12/1966 | Beucler |
| 3,373,915 A | 3/1968 | Anderson et al. |
| 3,420,360 A | 1/1969 | Young |
| 3,443,827 A | 5/1969 | Acker et al. |
| 3,456,645 A | 7/1969 | Brock |
| 3,479,561 A | 11/1969 | Janning |
| 3,567,014 A | 3/1971 | Feigelman |
| 3,675,661 A | 7/1972 | Weaver |
| 3,707,017 A | 12/1972 | Paquette |
| 3,792,704 A | 2/1974 | Parker |
| 3,815,597 A | 6/1974 | Gottelman |
| 3,861,523 A | 1/1975 | Fountain et al. |
| 3,941,300 A | 3/1976 | Troth |
| 4,020,853 A | 5/1977 | Nuttal |
| 4,049,005 A | 9/1977 | Hernandez et al. |
| 4,066,088 A | 1/1978 | Ensor |
| 4,207,976 A | 6/1980 | Herman |
| 4,215,708 A | 8/1980 | Bron |
| 4,219,032 A | 8/1980 | Tabatznik et al. |
| 4,303,083 A | 12/1981 | Burruss |
| 4,506,683 A | 3/1985 | Cantrell et al. |
| 4,519,319 A | 5/1985 | Howlett |
| 4,520,938 A | 6/1985 | Finke |
| 4,595,024 A | 6/1986 | Greene et al. |
| 4,648,393 A | 3/1987 | Landis et al. |
| 4,708,151 A | 11/1987 | Shelar |
| 4,735,217 A | 4/1988 | Gerth et al. |
| 4,771,796 A | 9/1988 | Myer |
| 4,793,365 A | 12/1988 | Sensabaugh, Jr. et al. |
| 4,794,323 A | 12/1988 | Zhou et al. |
| 4,798,310 A | 1/1989 | Kasai et al. |
| 4,813,536 A | 3/1989 | Willis |
| 4,819,665 A | 4/1989 | Roberts et al. |
| 4,830,028 A | 5/1989 | Lawson et al. |
| 4,836,224 A | 6/1989 | Lawson et al. |
| 4,846,199 A | 7/1989 | Rose |
| 4,848,374 A | 7/1989 | Chard et al. |
| 4,848,563 A | 7/1989 | Robbins |
| 4,893,639 A | 1/1990 | White |
| 4,907,606 A | 3/1990 | Lilja et al. |
| 4,941,483 A | 7/1990 | Ridings |
| 4,944,317 A | 7/1990 | Thal |
| 4,947,874 A | 8/1990 | Brooks et al. |
| 4,947,875 A | 8/1990 | Brooks et al. |
| 5,005,759 A | 4/1991 | Bouche |
| 5,020,548 A | 6/1991 | Farrier et al. |
| 5,027,836 A | 7/1991 | Shannon et al. |
| 5,031,646 A | 7/1991 | Lippielio et al. |
| 5,050,621 A | 9/1991 | Creighton et al. |
| 5,060,671 A | 10/1991 | Counts et al. |
| 5,065,776 A | 11/1991 | Lawson et al. |
| 5,076,297 A | 12/1991 | Farrier et al. |
| 5,105,831 A | 4/1992 | Banerjee et al. |
| 5,105,838 A | 4/1992 | White et al. |
| 5,123,530 A | 6/1992 | Lee |
| 5,133,368 A | 7/1992 | Neumann et al. |
| 5,144,962 A | 9/1992 | Counts et al. |
| 5,152,456 A | 10/1992 | Ross et al. |
| 5,183,062 A | 2/1993 | Clearman et al. |
| 5,224,498 A | 7/1993 | Deevi et al. |
| 5,240,012 A | 8/1993 | Ehrman et al. |
| 5,249,586 A | 10/1993 | Morgan et al. |
| 5,261,424 A | 11/1993 | Sprinkel, Jr. |
| 5,269,237 A | 12/1993 | Baker et al. |
| 5,269,327 A | 12/1993 | Counts et al. |
| 5,303,720 A | 4/1994 | Banerjee et al. |
| 5,322,075 A | 6/1994 | Deevi et al. |
| 5,324,498 A | 6/1994 | Streusand et al. |
| 5,372,148 A | 12/1994 | McCafferty et al. |
| 5,388,574 A | 2/1995 | Ingebrethsen |
| 5,449,078 A | 9/1995 | Akers |
| 5,456,269 A | 10/1995 | Kollasch |
| 5,497,791 A | 3/1996 | Bowen et al. |
| 5,529,078 A | 6/1996 | Rehder et al. |
| 5,579,934 A | 12/1996 | Buono |
| 5,591,368 A | 1/1997 | Fleischhauer et al. |
| 5,605,226 A | 2/1997 | Hernlein |
| 5,641,064 A | 6/1997 | Goserud |
| 5,649,552 A | 7/1997 | Cho et al. |
| 5,666,977 A | 9/1997 | Higgins |
| 5,666,978 A | 9/1997 | Counts et al. |
| 5,708,258 A | 1/1998 | Counts et al. |
| 5,730,118 A | 3/1998 | Hermanson |

(56) References Cited

U.S. PATENT DOCUMENTS

| | | |
|---|---|---|
| 5,730,158 A | 3/1998 | Collins et al. |
| 5,746,587 A | 5/1998 | Racine et al. |
| 5,810,164 A | 9/1998 | Rennecamp |
| 5,819,756 A | 10/1998 | Mielordt |
| 5,845,649 A | 12/1998 | Saito et al. |
| 5,865,185 A | 2/1999 | Collins et al. |
| 5,881,884 A | 3/1999 | Podosek |
| 5,931,828 A | 8/1999 | Durkee |
| 5,934,289 A | 8/1999 | Watkins et al. |
| 5,938,018 A | 8/1999 | Keaveney et al. |
| 5,944,025 A | 8/1999 | Cook et al. |
| 5,994,025 A | 8/1999 | Cook et al. |
| 5,954,979 A | 9/1999 | Counts et al. |
| 5,967,310 A | 10/1999 | Hill |
| 5,975,415 A | 11/1999 | Zehnal |
| 5,979,460 A | 11/1999 | Matsumura |
| 5,996,589 A | 12/1999 | St. Charles |
| 6,053,176 A | 4/2000 | Adams |
| 6,089,857 A | 7/2000 | Matsuura et al. |
| 6,095,153 A | 8/2000 | Kessler et al. |
| 6,102,036 A | 8/2000 | Slutsky et al. |
| 6,125,853 A | 10/2000 | Susa et al. |
| 6,155,268 A | 12/2000 | Takeuchi |
| 6,164,287 A | 12/2000 | White |
| 6,196,232 B1 | 3/2001 | Chkadua |
| 6,234,169 B1 | 5/2001 | Bulbrook et al. |
| 6,269,966 B1 | 8/2001 | Pallo et al. |
| 6,324,261 B1 | 11/2001 | Merte |
| 6,349,728 B1 | 2/2002 | Pham |
| 6,381,739 B1 | 4/2002 | Breternitz, Jr. et al. |
| 6,386,371 B1 | 5/2002 | Parsons |
| 6,431,363 B1 | 8/2002 | Hacker |
| 6,446,793 B1 | 9/2002 | Layshock |
| 6,510,982 B2 | 1/2003 | White et al. |
| 6,532,965 B1 | 3/2003 | Abhulimen et al. |
| 6,536,442 B2 | 3/2003 | St. Charles et al. |
| 6,557,708 B2 | 5/2003 | Polacco |
| 6,598,607 B2 | 7/2003 | Adiga et al. |
| 6,603,924 B2 | 8/2003 | Brown et al. |
| 6,606,998 B2 | 8/2003 | Gold |
| 6,612,404 B2 | 9/2003 | Sweet et al. |
| 6,615,840 B1 | 9/2003 | Fournier et al. |
| 6,622,867 B2 | 9/2003 | Menceles |
| 6,655,379 B2 | 12/2003 | Clark et al. |
| 6,672,762 B1 | 1/2004 | Faircloth et al. |
| 6,688,313 B2 | 2/2004 | Wren et al. |
| 6,726,006 B1 | 4/2004 | Funderburk et al. |
| 6,772,756 B2 | 8/2004 | Shayan |
| 6,799,576 B2 | 10/2004 | Farr |
| 6,803,545 B2 | 10/2004 | Blake et al. |
| 6,805,545 B2 | 10/2004 | Slaboden |
| 6,810,883 B2 | 11/2004 | Felter et al. |
| 6,827,573 B2 | 12/2004 | St. Charles et al. |
| 6,954,979 B2 | 10/2005 | Logan |
| 7,000,775 B2 | 2/2006 | Gelardi et al. |
| 7,015,796 B2 | 3/2006 | Snyder |
| 7,434,584 B2 | 10/2008 | Steinberg |
| 7,488,171 B2 | 2/2009 | St. Charles et al. |
| D590,990 S | 4/2009 | Hon |
| D590,991 S | 4/2009 | Hon |
| 7,546,703 B2 | 6/2009 | Johnske et al. |
| 7,621,403 B2 | 11/2009 | Althoff et al. |
| 7,644,823 B2 | 1/2010 | Gelardi et al. |
| 7,726,320 B2 * | 6/2010 | Robinson et al. .... A24F 47/008 131/194 |
| 7,767,698 B2 | 8/2010 | Warchol et al. |
| 7,801,573 B2 | 9/2010 | Yazdi et al. |
| 7,815,332 B1 | 10/2010 | Smith |
| 7,832,410 B2 | 11/2010 | Hon |
| 7,886,507 B2 | 2/2011 | McGuinness, Jr. |
| 7,988,034 B2 | 8/2011 | Pezzoli |
| 8,156,944 B2 | 4/2012 | Hon |
| 8,251,060 B2 | 8/2012 | White et al. |
| 8,322,350 B2 | 12/2012 | Lipowicz |
| 8,371,310 B2 | 2/2013 | Brenneise |
| 8,381,739 B2 | 2/2013 | Gonda |
| 8,387,612 B2 | 3/2013 | Damani et al. |
| 8,511,318 B2 | 8/2013 | Hon |
| 8,541,401 B2 | 9/2013 | Mishra et al. |
| 8,671,952 B2 | 3/2014 | Winterson et al. |
| 8,741,348 B2 | 6/2014 | Hansson et al. |
| 8,809,261 B2 | 8/2014 | Elsohly et al. |
| 8,851,081 B2 | 10/2014 | Fernando et al. |
| 8,915,254 B2 | 12/2014 | Monsees et al. |
| 8,925,555 B2 | 1/2015 | Monsees et al. |
| 8,991,402 B2 | 3/2015 | Monsees et al. |
| 9,215,895 B2 | 12/2015 | Bowen et al. |
| 2001/0015209 A1 | 8/2001 | Zielke |
| 2001/0032643 A1 | 10/2001 | Hochrainer et al. |
| 2001/0032795 A1 | 10/2001 | Weinstein et al. |
| 2001/0052480 A1 | 12/2001 | Kawaguchi et al. |
| 2002/0078951 A1 | 6/2002 | Nichols et al. |
| 2002/0175164 A1 | 11/2002 | Dees et al. |
| 2003/0005926 A1 | 1/2003 | Jones et al. |
| 2003/0089377 A1 | 5/2003 | Hajaligol et al. |
| 2003/0150451 A1 | 8/2003 | Shayan |
| 2003/0154991 A1 | 8/2003 | Fournier et al. |
| 2004/0031495 A1 | 2/2004 | Steinberg |
| 2004/0050382 A1 | 3/2004 | Goodchild |
| 2004/0099266 A1 | 5/2004 | Cross et al. |
| 2004/0149296 A1 | 8/2004 | Rostami et al. |
| 2004/0149624 A1 | 8/2004 | Wischusen et al. |
| 2004/0173229 A1 | 9/2004 | Crooks et al. |
| 2004/0182403 A1 | 9/2004 | Andersson et al. |
| 2004/0221857 A1 | 11/2004 | Dominguez |
| 2004/0237974 A1 | 12/2004 | Min |
| 2005/0016549 A1 | 1/2005 | Banerjee et al. |
| 2005/0016550 A1 | 1/2005 | Katase |
| 2005/0034723 A1 | 2/2005 | Bennett et al. |
| 2005/0061759 A1 | 3/2005 | Doucette |
| 2005/0069831 A1 | 3/2005 | St. Charles et al. |
| 2005/0090798 A1 | 4/2005 | Clark et al. |
| 2005/0118545 A1 | 6/2005 | Wong |
| 2005/0145533 A1 | 7/2005 | Seligson |
| 2005/0172976 A1 | 8/2005 | Newman et al. |
| 2005/0244521 A1 | 11/2005 | Strickland et al. |
| 2005/0268911 A1 | 12/2005 | Cross et al. |
| 2006/0018840 A1 | 1/2006 | Lechuga Ballesteros et al. |
| 2006/0054676 A1 | 3/2006 | Wischusen |
| 2006/0102175 A1 | 5/2006 | Nelson |
| 2006/0150991 A1 | 7/2006 | Lee |
| 2006/0191546 A1 | 8/2006 | Takano et al. |
| 2006/0191548 A1 | 8/2006 | Strickland et al. |
| 2006/0196518 A1 | 9/2006 | Hon |
| 2006/0254948 A1 | 11/2006 | Herbert et al. |
| 2006/0255105 A1 | 11/2006 | Sweet |
| 2007/0006889 A1 | 1/2007 | Kobal et al. |
| 2007/0045288 A1 | 3/2007 | Nelson |
| 2007/0062548 A1 | 3/2007 | Horstmann et al. |
| 2007/0074734 A1 | 4/2007 | Braunshteya et al. |
| 2007/0098148 A1 | 5/2007 | Sherman |
| 2007/0102013 A1 | 5/2007 | Adams et al. |
| 2007/0144514 A1 | 6/2007 | Yeates et al. |
| 2007/0163610 A1 | 7/2007 | Lindell et al. |
| 2007/0215164 A1 | 9/2007 | Mehio |
| 2007/0235046 A1 | 10/2007 | Gedevanishvili |
| 2007/0267033 A1 | 11/2007 | Mishra et al. |
| 2007/0277816 A1 | 12/2007 | Morrison et al. |
| 2007/0280652 A1 | 12/2007 | Williams |
| 2007/0283972 A1 | 12/2007 | Monsees et al. |
| 2008/0000763 A1 | 1/2008 | Cove |
| 2008/0023003 A1 | 1/2008 | Rosenthal |
| 2008/0029095 A1 | 2/2008 | Esser |
| 2008/0092912 A1 | 4/2008 | Robinson et al. |
| 2008/0149118 A1 | 6/2008 | Oglesby et al. |
| 2008/0216828 A1 | 9/2008 | Wensley et al. |
| 2008/0241255 A1 | 10/2008 | Rose et al. |
| 2008/0257367 A1 | 10/2008 | Paterno et al. |
| 2008/0276947 A1 | 11/2008 | Martzel |
| 2009/0004249 A1 | 1/2009 | Gonda |
| 2009/0095287 A1 | 4/2009 | Emarlou |
| 2009/0111287 A1 | 4/2009 | Lindberg et al. |
| 2009/0126745 A1 | 5/2009 | Hon |
| 2009/0133691 A1 | 5/2009 | Yamada et al. |

(56) References Cited

U.S. PATENT DOCUMENTS

| | | |
|---|---|---|
| 2009/0133703 A1 | 5/2009 | Strickland et al. |
| 2009/0133704 A1 | 5/2009 | Strickland et al. |
| 2009/0151717 A1 | 6/2009 | Bowen |
| 2009/0230117 A1 | 9/2009 | Fernando et al. |
| 2009/0255534 A1 | 10/2009 | Paterno |
| 2009/0260641 A1 | 10/2009 | Monsees |
| 2009/0260642 A1 | 10/2009 | Monsees |
| 2009/0267252 A1 | 10/2009 | Ikeyama |
| 2009/0272379 A1 | 11/2009 | Thorens |
| 2009/0283103 A1 | 11/2009 | Nielsen et al. |
| 2009/0288668 A1 | 11/2009 | Inagaki |
| 2009/0288669 A1 | 11/2009 | Hutchens |
| 2009/0293892 A1 | 12/2009 | Williams et al. |
| 2009/0293895 A1 | 12/2009 | Axelsson et al. |
| 2010/0000672 A1 | 1/2010 | Fogle |
| 2010/0006092 A1 | 1/2010 | Hale |
| 2010/0024834 A1 | 2/2010 | Oglesby et al. |
| 2010/0031968 A1 | 2/2010 | Sheikh |
| 2010/0163063 A1 | 7/2010 | Fernando et al. |
| 2010/0186757 A1 | 7/2010 | Crooks et al. |
| 2010/0236562 A1 | 9/2010 | Hearn et al. |
| 2010/0242976 A1 | 9/2010 | Katayama et al. |
| 2010/0275938 A1 | 11/2010 | Roth et al. |
| 2011/0036346 A1 | 2/2011 | Cohen et al. |
| 2011/0049226 A1 | 3/2011 | Moreau et al. |
| 2011/0094523 A1 | 4/2011 | Thorens et al. |
| 2011/0108023 A1 | 5/2011 | McKinney |
| 2011/0192397 A1 | 8/2011 | Saskar et al. |
| 2011/0226236 A1 | 9/2011 | Buchberger |
| 2011/0226266 A1 | 9/2011 | Tao |
| 2011/0232654 A1 | 9/2011 | Mass |
| 2011/0236002 A1 | 9/2011 | Oglesby et al. |
| 2012/0247494 A1 | 10/2012 | Oglesby et al. |
| 2012/0260927 A1 | 10/2012 | Liu |
| 2013/0042865 A1 | 2/2013 | Monsees |
| 2013/0068239 A1 | 3/2013 | Youn |
| 2013/0152922 A1 | 6/2013 | Benassayag et al. |
| 2013/0312742 A1 | 11/2013 | Monsees |
| 2014/0041655 A1 | 2/2014 | Barron |
| 2014/0060552 A1 | 3/2014 | Cohen et al. |
| 2014/0345631 A1 | 11/2014 | Bowen et al. |
| 2014/0366898 A1 | 12/2014 | Monsees |
| 2014/0378790 A1 | 12/2014 | Cohen |
| 2015/0150308 A1 | 6/2015 | Monsees et al. |
| 2015/0208729 A1 | 7/2015 | Monsees et al. |
| 2016/0044967 A1 | 2/2016 | Bowen et al. |
| 2016/0044968 A1 | 2/2016 | Bowen et al. |
| 2016/0174611 A1 | 6/2016 | Monsees et al. |

FOREIGN PATENT DOCUMENTS

| | | |
|---|---|---|
| CN | 1122213 A | 5/1996 |
| CN | 1333657 A | 1/2002 |
| CN | 1633247 A | 6/2005 |
| CN | 301472873 S | 2/2011 |
| CN | 302002622 S | 7/2012 |
| CN | 302292447 S | 1/2013 |
| CN | 302311408 S | 1/2013 |
| DE | 4200639 | 7/1992 |
| DE | 19854005 A1 | 5/2000 |
| DE | 19854012 A1 | 5/2000 |
| EP | 0295122 A2 | 12/1988 |
| EP | 0311581 A1 | 4/1989 |
| EP | 0430559 A2 | 6/1991 |
| EP | 0503767 A1 | 9/1992 |
| EP | 0532194 A1 | 3/1993 |
| EP | 0535695 | 4/1993 |
| EP | 0283672 B1 | 9/1993 |
| EP | 1458388 A | 9/2004 |
| EP | 2152313 B1 | 9/2014 |
| EP | 2772148 | 9/2014 |
| EP | 2319934 B1 | 9/2015 |
| ES | 2118034 A1 | 9/1998 |
| GB | 1025630 A | 4/1966 |
| GB | 1065678 | 4/1967 |
| IE | S2005-0051 | 2/2005 |
| IE | S2005-0563 | 8/2005 |
| IE | S2005-0615 | 9/2005 |
| JP | 61-108364 | 5/1986 |
| JP | 62-278975 | 12/1987 |
| JP | 64-37276 A | 2/1989 |
| JP | 2-124082 | 5/1990 |
| JP | 02-145179 A | 6/1990 |
| JP | 03-049671 | 4/1991 |
| JP | 03-180166 | 6/1991 |
| JP | 05-115272 | 5/1993 |
| JP | 1993-115272 | 5/1993 |
| JP | 09-075058 | 3/1997 |
| JP | 10-501999 A | 2/1998 |
| JP | 11-178563 | 6/1999 |
| JP | 2000-203639 | 7/2000 |
| JP | 2000-236865 | 9/2000 |
| JP | 2001-165437 A | 6/2001 |
| JP | 1991-232481 | 10/2001 |
| JP | 2002-529111 | 9/2002 |
| JP | 2005-034021 A | 2/2005 |
| JP | 2005-506080 | 3/2005 |
| JP | 2006-504430 | 2/2006 |
| KR | 10-0193885 B1 | 6/1999 |
| WO | WO 95/01137 A1 | 1/1995 |
| WO | WO97/12639 A1 | 4/1997 |
| WO | WO-2000/28842 A1 | 5/2000 |
| WO | WO-2001/82725 A1 | 11/2001 |
| WO | WO-2003/056948 A1 | 7/2003 |
| WO | WO 2003/070031 A1 | 8/2003 |
| WO | WO03/082031 A1 | 10/2003 |
| WO | WO03/094900 A1 | 11/2003 |
| WO | WO 03/103387 A2 | 12/2003 |
| WO | WO 2004/041006 A1 | 5/2004 |
| WO | WO 2004/064548 A1 | 8/2004 |
| WO | WO2004/080216 A1 | 9/2004 |
| WO | WO-2005/020726 A1 | 3/2005 |
| WO | WO-2006/015070 | 2/2006 |
| WO | WO-2006/082571 A1 | 8/2006 |
| WO | WO-2007/012007 A2 | 1/2007 |
| WO | WO-2007/026131 | 3/2007 |
| WO | WO-2007/039794 A2 | 4/2007 |
| WO | WO-2007/042941 | 4/2007 |
| WO | WO2007/078273 A1 | 7/2007 |
| WO | WO2008/077271 A1 | 7/2008 |
| WO | WO-2009/079641 A2 | 6/2009 |
| WO | WO-2009/079641 A3 | 6/2009 |
| WO | WO2010/023561 A1 | 3/2010 |
| WO | WO 2013/025921 A1 | 2/2013 |
| WO | WO-2014/201432 | 12/2014 |
| WO | WO2015/084544 A1 | 6/2015 |
| WO | WO2015/175979 A1 | 11/2015 |

OTHER PUBLICATIONS

Monsees et al.; U.S. Appl. No. 15/368,539 entitled "Low temperature electronic vaporization device and methods," filed Dec. 2, 2016.

Bowen et al.; U.S. Appl. No. 15/309,554 entitled "Systems and methods for aerosolizing a smokeable material," filed Nov. 8, 2016.

Monsees et al.; U.S. Appl. No. 15/379,898 entitled "Vaporization device systems and methods," filed Dec. 15, 2016.

Hatton et al.; U.S. Appl. No. 15/396,584 entitled "Leak-resistant vaporizer cartridges for use with cannabinoids," filed Dec. 31, 2016.

Burch et al.; Effect of pH on nicotine absorption and side effects produced by aerosolized nicotine; Journal of Aerosol Medicine: Deposition, Clearance, and Effects in the Lung; 6(1); pp. 45-52; 1993.

Food & Drug Administration; Warning letter to The Compounding Pharmacy; retrieved Oct. 10, 2014 from http://www.fda.gov/ICECI/EnfocementActions/WarningLetters/2002/ucm144843.htm; 3 pgs.; Apr. 9, 2002.

Harvest Vapor; American Blend Tobacco (product info.); retrieved from the internet (http://harvestvapor.com/); 2 pgs.; print/retrieval date: Oct. 10, 2014.

Inchem; Benzoic Acid; JECFA Evaluation Summary; retrieved Oct. 10, 2014 from http://www.inchem.org/documents/jecfa/feceval/jec_184.htm; 2 pgs..; May 28, 2005.

(56) References Cited

OTHER PUBLICATIONS

Inchem; Levulinic Acid; JECFA Evaluation Summary; retrieved Oct. 10, 2014 from http://www.inchem.org/documents/jecfa/feceval/jec_1266.htm; 1 pg.; Mar. 10, 2003.
Inchem; Pyruvic Acid; JECFA Evaluation Summary; retrieved Oct. 10, 2014 from http://www.inchem.org/documents/jecfa/feceval/jec_2072.htm; 1 pg.; Jan. 29, 2003.
Inchem; Sorbic Acid; JECFA Evaluation Summary; retrieved Oct. 10, 2014 from http://www.inchem.org/documents/jecfa/feceval/jec_2181.htm; 1 pg.; May 29, 2005.
Perfetti; Structural study of nicotine salts; Beitrage zur Tabakforschung International; Contributions to Tobacco Research; 12(2); pp. 43-54; Jun. 1983.
Seeman et al.; The form of nicotine in tobacco. Thermal transfer of nicotine and nicotine acid salts to nicotine in the gas phase; J Aric Food Chem.; 47(12); pp. 5133-5145; Dec. 1999.
Monsees et al.; U.S. Appl. No. 15/257,748 entitled "Cartridge for use with a vaporizer device," filed Sep. 6, 2016.
Monsees et al.; U.S. Appl. No. 15/257,760 entitled "Vaporizer apparatus," filed Sep. 6, 2016.
Monsees et al.; U.S. Appl. No. 15/257,768 entitled "Vaporizer apparatus," filed Sep. 6, 2016.
Monsees et al.; U.S. Appl. No. 15/261,823 entitled "Low temperature electronic vaporization device and methods," filed Sep. 9, 2016.
European Patent Application No. 12824116.3 Extended European Search Report dated Mar. 4, 2015.
"Lighter." Merriam-Webster Online Dictionary. 2009. Merriam-Webster Online. Jun. 8, 2009 [http://www.merriam-webster.com/dictionary/lighter].
Baker et al., "The pyrolysis of tobacco ingredients," J. Anal. Appl. Pyrolysis, vol. 71, pp. 223-311 (2004).
Bombick, et al. Chemical and biological studies of a new cigarette that primarily heats tobacco. Part 2. In vitro toxicology of mainstream smoke condensate. Food and Chemical Toxicology. 1997; 36:183-190.
Bombick, et al. Chemical and biological studies of a new cigarette that primarily heats tobacco. Part 3. In vitro toxicity of whole smoke. Food and Chemical Toxicology. 1998; 36:191-197.
Borgerding, et al. Chemical and biological studies of a new cigarette that primarily heats tobacco. Part 1. Chemical composition of mainstream smoke. Food and Chemical Toxicology. 1997; 36 169-182.
Davis & Nielsen, "Marketing, Processing and Storage: Green Leaf Threshing and Redrying Tobacco," Tobacco Production, Chemistry and Technology, (1999) Section 10B, pp. 330-333, Bill Ward, Expert Leaf Tobacco Company, Wilson, North Carolina, USA.
European Application No. 14153340.6 Search report and search opinion dated Oct. 8, 2014.
European Application No. 06787864.5 Extended European Search Report dated Mar. 22, 2013.
European Application No. 08860921.9 Extended Search Report dated Oct. 10, 2013.
European Application No. 14153321.6 Office action dated May 22, 2014.
European Application No. 14153323.2 Office action dated May 22, 2014.
European Application No. 14153324.0 Office action dated May 22, 2014.
European Application No. 14153327.3 Search report dated May 26, 2014.
European Application No. 14153326.5 Office action dated May 27, 2014.
European Application No. 14153323.2 Communication dated Jan. 29, 2015.
European Application No. 14153326.5 Communication dated Jan. 29, 2015.
European Application No. 14153321.6 Communication dated Jan. 28, 2015.
European Application No. 14153327.3 Communication dated Jan. 30, 2015.
European Application No. 13189967.6 Search Report dated Jun. 13, 2014.
European Application No. 14153325.7 Search report dated Jun. 20, 2014.
European Application No. 14153327.3 Office action dated Jun. 27, 2014.
European Application No. 06787864.5 Exam Report dated Nov. 12, 2013.
European Application No. 14153324.0 Search report dated May 9, 2014.
European Application No. 14153326.5 Search Report dated May 9, 2014.
European Application No. 14153321.6 Search report dated May 9, 2014.
European Application No. 14153323.2 Search report dated May 9, 2014.
Ingebrethsen et al., "Electronic Cigarette aerosol particle size distribution measurements", Inhalation Toxicology, 2012; 24 (14): 976-984.
Kuo et al. Applications of Turbulent and Multiphase Combustion, Appendix D: Particle Size—U.S. Sieve Size and Tyler Screen Mesh Equivalents, 2012, p. 541-543.
McCann et al., "Detection of carcinogens as mutagens in the Salmonella/microsome test: Assay of 300 chemicals: discussion." Proct. Nat. Acad. Sci, USA, Mar. 1976, vol. 73 (3), 950-954.
Nicoli et al., Mammalian tumor xenografts induce neovascularization in Zebrafish embryos. Cancer Research, 67:2927-2931 (2007).
PCT/IB2006/002040 International Preliminary Report on Patentability dated Apr. 1, 2008.
PCT/IB2006/002040 International Search Report and Written Opinion dated Mar. 26, 2007.
PCT/IB2006/003842 International Preliminary Report on Patentability dated Apr. 1, 2008.
PCT/IB2006/003842 International Search Report and Written Opinion dated May 31, 2007.
PCT/US06/28039 Corrected Written Opinion dated Dec. 20, 2007.
PCT/US06/28039 International Search Report dated Sep. 6, 2007.
PCT/US06/28039 IPER and Written Opinion dated Jul. 15, 2008.
PCT/US08/87488 IPRP and Written Opinion dated Jun. 22, 2010.
PCT/US2008/87488 International Search Report dated Jul. 13, 2009.
PCT/US2008/87488 Written Opinion dated Jul. 13, 2009.
PCT/US2012/051165 International Preliminary Report on Patentability dated Feb. 18, 2014.
PCT/US2012/051165 International Search Report and Written Opinion dated Oct. 25, 2012.
PCT/US2014/042425 International Search Report and Written Opinion dated Nov. 3, 2014.
Torikai et al., "Effects of temperature, atmosphere and pH on the generation of smoke compounds during tobacco pyrolysis," Food and Chemical Toxicology 42 (2004) 1409-1417.
U.S. Appl. No. 11/485,168 Office Action dated Feb. 4, 2010.
U.S. Appl. No. 11/485,168 Office action dated Mar. 27, 2014.
U.S. Appl. No. 11/485,168 Office Action dated Jun. 23, 2009.
U.S. Appl. No. 11/485,168 Office action dated Jul. 9, 2014.
U.S. Appl. No. 11/485,168 Office Action dated Aug. 3, 2010.
U.S. Appl. No. 11/485,168 Office action dated Sep. 5, 2013.
U.S. Appl. No. 11/485,168 Office Action dated Nov. 3, 2009.
U.S. Appl. No. 11/485,168 Office action dated Dec. 21, 2012.
U.S. Appl. No. 12/336,439 Final Action dated Nov. 25, 2013.
U.S. Appl. No. 12/336,439 Final Office Action dated Feb. 1, 2012.
U.S. Appl. No. 12/336,439 Office action dated Aug. 6, 2014.
U.S. Appl. No. 12/336,439 Office Action dated Aug. 17, 2011.
U.S. Appl. No. 12/336,439 Office Action dated Feb. 22, 2013.
U.S. Appl. No. 12/336,439 Office Action dated Feb. 28, 2014.
U.S. Appl. No. 12/482,379 Final Office Action dated Sep. 5, 2012.
U.S. Appl. No. 12/482,379 Non Final Office Action dated Dec. 17, 2013.
U.S. Appl. No. 12/482,379 Office Action dated Dec. 22, 2011.
U.S. Appl. No. 13/587,416 Office Action dated Feb. 2, 2015.
U.S. Appl. No. 13/587,416 Office Action dated Oct. 31, 2014.
U.S. Appl. No. 29/446,987 Office Action dated Nov. 13, 2014.

(56) References Cited

OTHER PUBLICATIONS

Wells. "Glycerin as a Constituent of Cosmetics and Toilet Preparations." Journal of the Society of Cosmetic Chemists,1958; 9(1): 19-25.
European Patent Application No. 14153325.7 Office Action dated Feb. 23, 2015.
Monsees, J.; U.S. Appl. No. 12/115,400 entitled "Method And System for Vaporization of a Substance", filed May 5, 2008.
Bowen et al.; U.S. Appl. No. 14/960,259 entitled "Calibrated Dose Control", filed Dec. 4, 2015.
Monsees et al.; U.S. Appl. No. 15/165,954 entitled "Devices for vaporization of a substance," filed May 26, 2016.
Monsees et al.; U.S. Appl. No. 15/166,001 entitled "Electronic vaporization device," filed May 26, 2016.
Monsees et al.; U.S. Appl. No. 15/165,972 entitled "Portable devices for generating an inhalable vapor," filed May 26, 2016.
Bowen et al.; U.S. Appl. No. 15/101,303 entitled "Nicotine liquid formulations for aerosol devices and methods thereof," filed Jun. 2, 2016.

* cited by examiner

AEROSOL DEVICES AND METHODS FOR INHALING A SUBSTANCE AND USES THEREOF

CROSS-REFERENCE

This application is a continuation of U.S. application Ser. No. 12/336,439, filed Dec. 16, 2008, which claims the benefit of U.S. Provisional Application No. 61/014,690, filed Dec. 18, 2007, which application is incorporated herein by reference.

BACKGROUND OF THE INVENTION

The use of tobacco products and the harmful side effects of smoking tobacco continue to gain increasing attention worldwide. As more regulations come into effect regarding smoking in the work place or in public, interest in developing alternative products is growing significantly. One method of reducing the harmful side effects of smoking is to not burn the tobacco products. This is because many of the harmful analytes, such as Hoffman analytes, obtained from smoking are received due to the burning of the material.

A difficulty of developing and marketing a device that can deliver an aerosolized tobacco product is catering to the user in terms of visual and physical appeal of use. A device that can be used multiple times to aerosolize a variety of different substances while providing similar sensations to the user as those from smoking, such as visual vapor, are desirable. A device and product that can aerosolize a tobacco product and reduce Hoffman analytes and mutagenic compounds delivered to a user as compared to smoking are also desirable.

SUMMARY OF THE INVENTION

In an aspect of the invention, a cartridge is disclosed for use in a device for aerosolizing a material comprising: a shell for containing a viscous vaporizable material; and a lid sealed upon the shell, thereby forming a sealed cartridge containing the viscous vaporizable material. The lid can be penetrable, wherein a penetrated lid allows an exit of an aerosol generated from heating the viscous vaporizable material. The lid can also be a heat-sealable film, wherein the heat-sealable film comprises a base layer and a heat-sealable layer. The shell of the cartridge or the lid of the cartridge can comprise aluminum. When a shell of a cartridge of the invention comprises a flange, a lid can be sealed upon the flange.

The cartridge can be heated to a temperature required to aerosolize the material contained within the shell, preferably heated to a temperature less than 400° F. The viscous vaporizable material within the cartridge can comprise at least one of an aerosol-forming medium, propylene glycol and glycerin. The viscous vaporizable material can comprise tobacco.

The cartridge can be inserted into a device wherein the device is capable of aerosolizing the viscous vaporizable material. The device can comprise an oven chamber capable of heating the cartridge.

In order to mark a cartridge of the invention, information can be printed on at least one of the shell and the lid.

In another aspect, a method of filling a cartridge containing a viscous vaporizable material comprises: loading the viscous vaporizable material into a shell of the cartridge; and sealing a lid on the shell of the cartridge. The method can be automated, for example, carried out on a linear or rotating indexing machine, or loaded using an auger filler, peristaltic pump or piston pump method. A predetermined volume of viscous vaporizable material can be loaded in the loading step, wherein the predetermined volume can be about 0.1 to about 0.8 cubic centimeters. Preferably, the volume is about 0.25 cubic centimeters. The sealing step of a method of filling the cartridge can comprise heating at least one of the lid and the shell of the cartridge and trimming any excess material from the lid.

A device for generating an inhalable aerosol is provided herein comprising: a body; a heater within said body capable of heating a viscous vaporizable material to generate an inhalable aerosol; and temperature regulator comprising one or more bimetallic discs, wherein the discs convert a temperature change into mechanical displacement. The inhalable aerosol can comprise particles less than about 2 microns in diameter. The heater of the device can be supplied by gaseous fuel, such as butane, and can be ignited by a piezoelectric igniter.

The discs of the temperature regulator can displace a pushrod that limits or ceases flow of the gaseous fuel within the body of the device by pushing on a variable flow-restricting valve. The pushrod can also provide support for a catalytic mesh element.

In another aspect, the invention provides a device which emulates smoking wherein the device generates an aerosol for inhalation by a subject by heating a viscous material containing plant matter to about 150° C. and wherein the aerosol has a tactile response in the mouth or respiratory tract. The viscous material can comprise an aerosol-forming medium that can comprise at least one of propylene glycol and glycerin to produce a visual aerosol when heated. The viscous material can also comprise tobacco and flavorants.

The device can also deliver an active element to a user that is part of the aerosol. The active element can be absorbed in the respiratory tract. The aerosol can comprise particles less than about 2 microns in diameter.

Disclosed herein is a device of the invention comprising a body and a heater wherein the device generates a smokeless aerosol for inhalation by a subject by heating a viscous tobacco material to a target temperature. The viscous material can comprise an aerosol-forming medium that can comprise at least one of propylene glycol and glycerin to produce a visual aerosol when heated. The device can deliver an active element to a user that is part of the aerosol. The active element can be absorbed in the respiratory tract. The aerosol can comprise particles less than about 2 microns in diameter.

The target temperature for heating the viscous material in the device can be about 100° C. to about 200° C. Preferably, the target temperature is about 150° C.

The device can also be operated by a user with a single hand.

In another aspect of the invention, an aerosol generating device is disclosed wherein the device generates an aerosol substantially free from at least one Hoffman analyte upon heating a smokable material to a target temperature. The Hoffman analyte can be selected from the group consisting of: ammonia, aminonaphthalenes, benzopyrene, formaldehyde, acetaldehyde, acetone, methyl ethyl ketone, butyraldehyde, hydrogen cyanide, nitrous oxides, tobacco-specific nitrosamines (TSNAs), pyridine, quinoline, hydroquinone, phenol, cresols, tar, nicotine, carbon monoxide, 1,3-butadiene, isoprene, acrylonitrile, benzene, toluene, and styrene.

The target temperature for heating the viscous material in the device can be about 100° C. to about 200° C. Preferably, the target temperature is about 150° C., which generates an aerosol comprising particles less than about 2 microns in diameter.

The invention also provides an aerosol generating device wherein the device generates an aerosol upon heating a smokable material to a target temperature with at least 70% less Hoffman analytes than a common tobacco cigarette, and wherein the Hoffman analyte can be selected from the group consisting of: ammonia, aminonaphthalenes, benzopyrene, formaldehyde, acetaldehyde, acetone, methyl ethyl ketone, butyraldehyde, hydrogen cyanide, nitrous oxides, tobacco-specific nitrosamines (TSNAs), pyridine, quinoline, hydroquinone, phenol, cresols, tar, nicotine, carbon monoxide, 1,3-butadiene, isoprene, acrylonitrile, benzene, toluene, and styrene. The common tobacco cigarette can comprise a filter.

The target temperature for heating the viscous material in the device can be about 100° C. to about 200° C. Preferably, the target temperature is about 150° C. and generates an aerosol comprising particles less than about 2 microns in diameter.

In an aspect, the invention discloses a method of delivering an aerosol substantially free from a Hoffman analyte to a subject comprising: deploying an aerosol generating device containing a heater and a smokable material; heating the smokable material with the heater of the device to a target temperature to generate an aerosol; and delivering the aerosol to the subject for inhalation.

In another aspect, a method of creating a tactile response in the mouth or respiratory tract is disclosed. The method comprises: deploying a smoke emulating device wherein the device generates a smokeless aerosol having a tactile response in the mouth or respiratory tract by heating a viscous material containing plant matter contained therein; heating the viscous material to a target temperature; generating an aerosol having the tactile response in the mouth or respiratory tract from the heated viscous material; and inhaling the aerosol. The viscous material can comprise an aerosol-forming medium that can comprise at least one of propylene glycol and glycerin to produce a visual aerosol when heated. The viscous material can also comprise at least one of tobacco and flavorants. The device can deliver an active element to a user that is part of the aerosol. The active element can be absorbed in the respiratory tract. The aerosol can comprise particles less than about 2 microns in diameter.

In another aspect, the invention discloses an aerosol generating device wherein the device generates an aerosol from a smokable material wherein the aerosol contains at least 70% less Hoffman analytes than a substance generated by burning the smokable material is provided by the invention.

Also disclosed is an aerosol generating device wherein the device generates an aerosol from a smokable material that passes the Ames test, and an aerosol generating device wherein the device generates an aerosol from a smokable material wherein the aerosol scores significantly better on the Ames test than a substance generated by burning the smokable material.

The invention provides an aerosol generating device wherein the device provides an aerosol for inhalation to a user for at least 4 non-continuous hours without replenishing fuel or otherwise servicing the device.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are used, and the accompanying drawings of which.

DETAILED DESCRIPTION OF THE INVENTION

The invention described herein has a wide range of applications for inhalation of an active substance as will be appreciated by persons of skill in the art upon reviewing the disclosure. For example, the devices, cartridges, systems, kits and methods could be used, for example, to inhale a tobacco product through the mouth or nose. The devices, cartridge, systems, kits, and methods could also be used to reduce the Hoffmann analytes provided to user by inhaling a tobacco product, as compared to smoking or burning of tobacco. Additionally, the devices, systems, kits and methods could be used, for example, to inhale any substance, such as a botanical, pharmaceutical, nutraceutical, or any other substance providing a benefit or sensation to an end user.

I. Aerosol Generating Device

Figure 1:
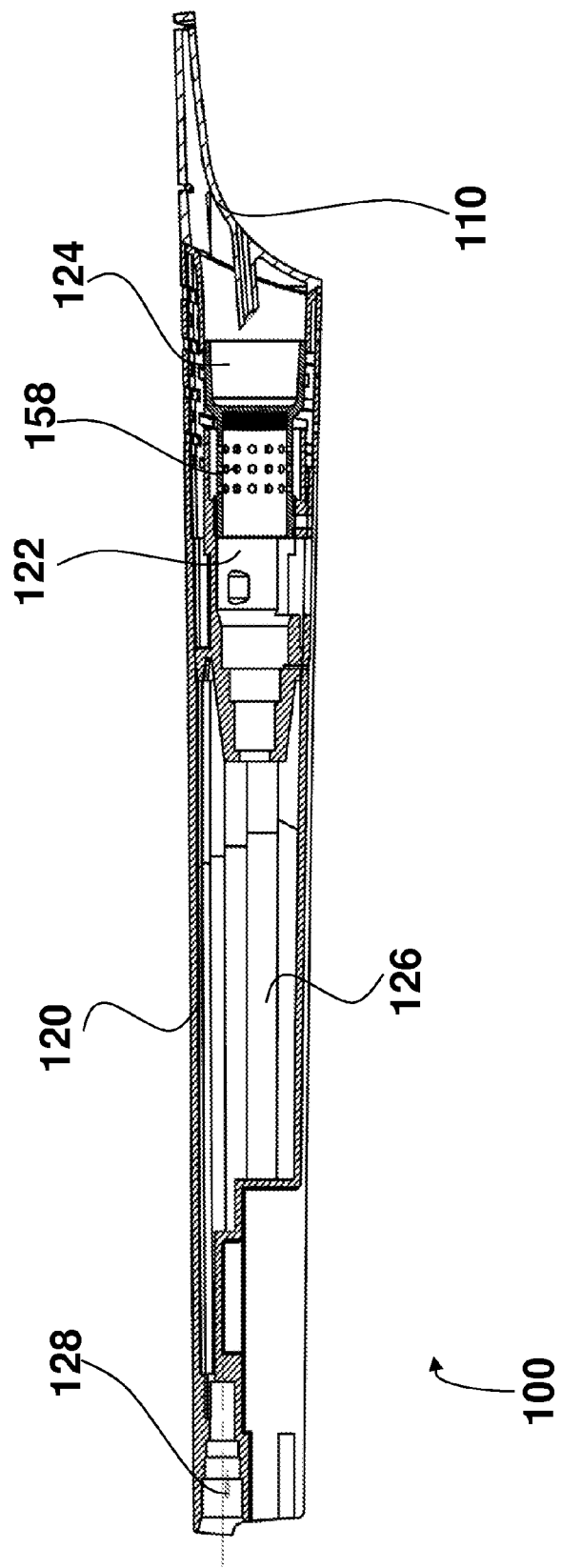
FIG. 1 illustrates a device of the invention comprising a mouthpiece and a body having a heater, an oven chamber, a fuel tank, and an igniter with controller for maintaining the operating temperature.

An exemplary device of the invention is illustrated in FIG. 1. The device 100 is capable of creating temperatures high enough to aerosolize a product contained within the device 100. A device of the invention can comprise a mouthpiece 110 and a body 120 having a heater 122, an oven chamber 124, a fuel tank 126, and an igniter with controller for maintaining the operating temperature. Examples of operating temperature regulators of a device include a bimetallic actuator. Alternatively, a paraffin-filled component that expands and contracts to modulate butane flow could be employed. Alternatively, a system could be employed to measure the current temperature, for example, with a thermocouple sensor and compare it to a prescribed temperature, for example, with a micro-controller, and by controlling an electromechanical valve, for example, servo or solenoid valve. A user-selected temperature, as described above, the selected temperature could be used as an input to this system.

A device can be constructed without an active regulating element. This can result in reduced complexity and in lowering the overall cost of manufacture of the device. For example, the flow of fuel to the heater 122 can be set at a low level. In use, the temperature inside the oven chamber 124 increases until an equilibrium point where additional heat introduced equals the heat lost to the environment. Heat is lost by conduction through the body of the device 100, and with the vapor delivered to the user. This equilibrium point determines the operating temperature of the device 100. By changing the fuel flow rate, size and material of the burner, and other factors, the system can be calibrated to provide a fairly stable desired operating temperature.

A piezo-electric igniter can be used. Other igniters can be used, such as, a flint starter or battery-powered resistive coil.

Figure 2:
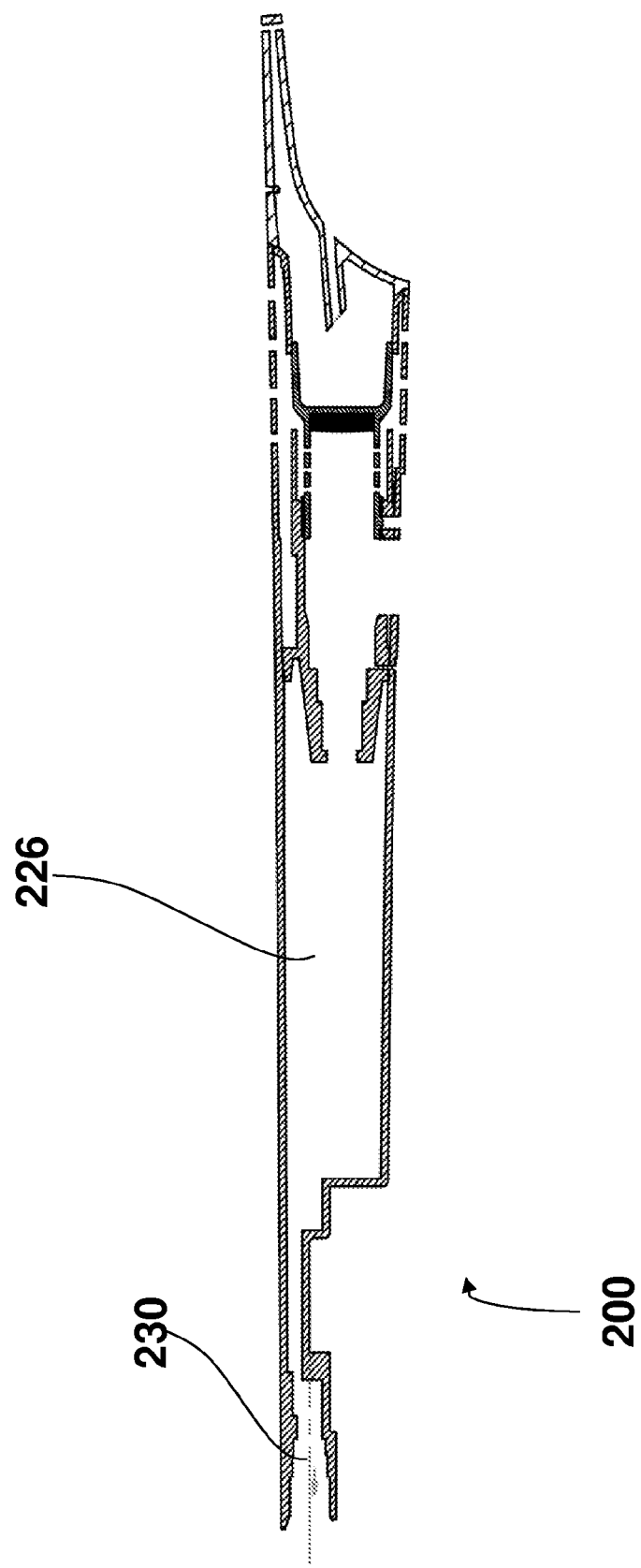
FIG. 2 illustrates a device of the invention comprising a fuel tank that is meant to be refillable, and has a port for that purpose.

As illustrated in FIG. 2, a device 200 of the invention can also comprise a fuel tank 226 that is meant to be refillable, and has a port 230 for that purpose. The tank 226 can be disposable once its fuel is exhausted. A release mechanism such as a pin or cam can be employed allowing the user to quickly remove the depleted tank 226 and replace it with a full tank. A replaceable tank might include additional parts of the device such as the igniter and heater. A liquid fuel is the preferable fuel source, however the liquid fuel can be complimented or replaced by a battery-powered electric heater or other compact heat source. The tank 126 can be filled by a fill valve mechanism 128 as shown in FIG. 1 with a specialized fuel source or a standard commercial fuel source.

The fuel tank can hold enough fuel for repeated uses of the device. The device can be used for up to 10, 20, 30, 40, 50, or 60 uses. In some embodiments, the device can be used for more than 60 uses. The device can also be used for up to 1, 2, 3, 4, 5, 6, 7, or 8 hours of continuous or non-continuous use. A cartridge for use with the device can be disposed after each use or used for multiple uses. The long lasting use of a device of the invention provides the user the advantage of not having to service the device or refill the fuel tank on a regular basis. The advantage of multiple uses can be preferably obtained by using a larger sized fuel tank and/or the use of butane as a fuel, which can produce the necessary temperatures to use the device in an efficient manner.

Typically, the operating temperatures of the device are no more than 200° C. Often the temperature required to aerosolize a product is between about 100 to 200° C. In some embodiments, the temperature required to aerosolize a product is about 150° C. Once the product within the device has been aerosolized, the aerosolized product is provided to a user through a mouthpiece. In many cases, a device of the invention is designed to emulate a smoking device, such as a cigarette, a pipe or a cigar holder.

Figure 3:
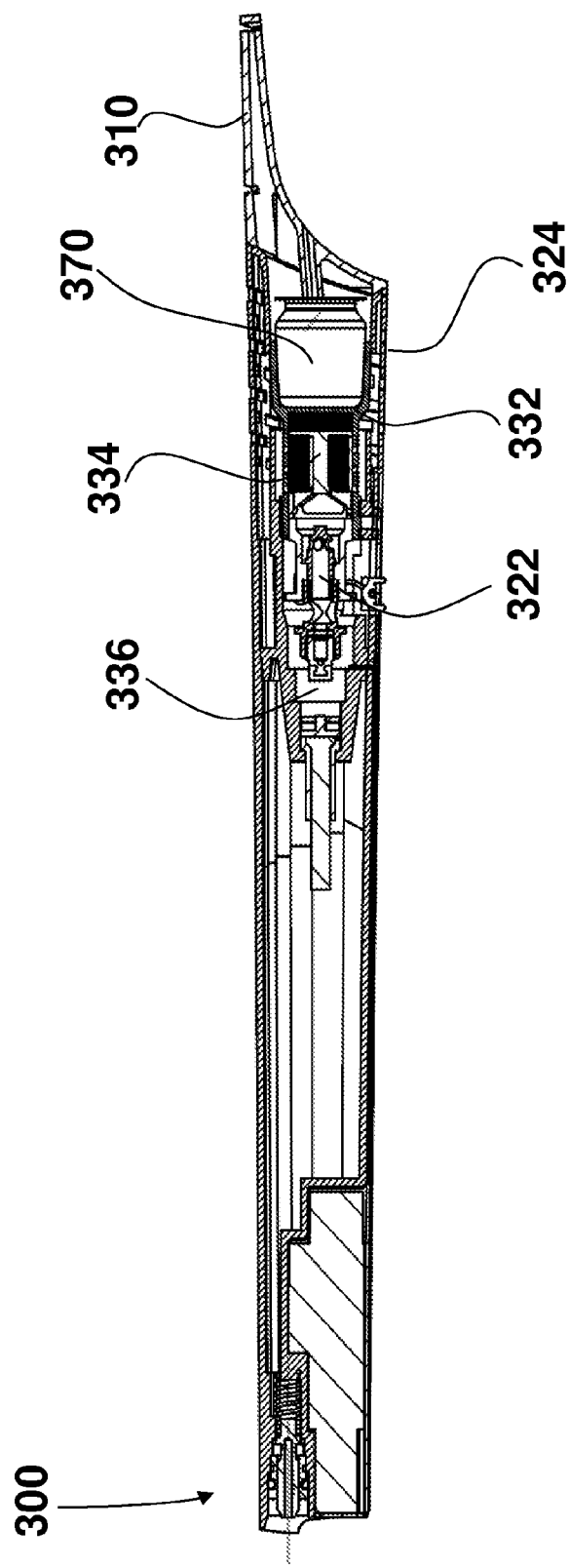
FIG. 3 illustrates a device of the invention comprising a heater assembly, which can be powered by any combustible fuel, and a series of bimetallic objects to control the flow of the combustible fuel to heater assembly.

In FIG. 3, the device 300 comprises a heater assembly 322, which can be powered by any combustible fuel, and a series of bimetallic objects 332 to control the flow of the combustible fuel to heater assembly 322. Examples of combustible fuel include, but are not limited to, propane, butane, methane, and ethanol. As the device 300 heats up, or a portion of the device 300 heats up, the bimetallic objects 332 change their shape (for example, from flat to concave or convex) in order to regulate the amount of fuel entering the heater assembly 322. This can occur by variety of mechanisms, including pushing a rod 334 (pushrod 334 as referred to herein) against a variable flow valve 336 as shown in FIG. 3.

A bimetallic object can be used to convert a temperature change into mechanical displacement. The object comprises two different metals which expand at different rates as they are heated, for example, steel and copper. The object can be an alloy or two metals that have been secured together. The bimetallic objects can be of any planar shape, such as a square, rectangle, or strip. Preferably, the bimetallic objects are bimetallic discs. The different expansions force the flat object to bend one way if heated, and to bend in the opposite direction if cooled. The bimetallic objects can be bimetallic discs such as the commercially available Truflex P675/700 discs.

The mechanical displacement of a bimetallic object is much larger than the small lengthways expansion in either of the two metals. This effect is used in a range of mechanical and electrical devices. In most of the example devices of the invention, the bimetallic object is used in the planar form. In others, it can be wrapped into a coil for compactness.

Nickel titanium (NiTi) is a shape memory alloy also commonly referred as Nitinol. Above its transformation temperature, Nitinol is superelastic and able to withstand a large amount of deformation when a load is applied and return to its original shape when the load is removed. Below its transformation temperature, it displays the shape memory effect. When it is deformed it will remain in that shape until heated above its transformation temperature, at which time it will return to its original shape. Nitinol is typically composed of approximately 55% Nickel by weight. Making small changes in the composition can change the transition temperature of the alloy significantly. These unique properties and tailorability of Nitinol to be used in a wide range of temperatures makes it suitable as substitute for the bimetallic object of the present invention. As will be appreciated by those skilled in the art other shape memory alloys can be used without departing from the scope of the invention.

The use of alternately-stacked bimetallic discs in a device of the invention is not only a simple and cheap solution for fitting a thermal regulation scheme into a very small space, but also has some key advantages over other methods of thermal regulation. The discs are a modular solution, meaning that different numbers of discs can be used to tune the temperature sensitivity of a device. Using multiple discs instead of one disc allows longer overall travel for a given (small) diameter of disk. Thinner or thicker discs can also be used for the same purpose, or to add additional ability to exert force. Since the doming shape of the discs is particularly strong, the varying pressure of the fuel will have minimal effect on the regulation temperature. Also, since the bimetallic stack is a non-discrete, continuously acting system, the device can have a dampened regulation effect by using the roughened-seat design mentioned above, making the device much less likely to self-extinguish. The discs also respond to a temperature at a point nearest the oven of the device so that the oven is held at the most constant temperature possible.

Figure 4:
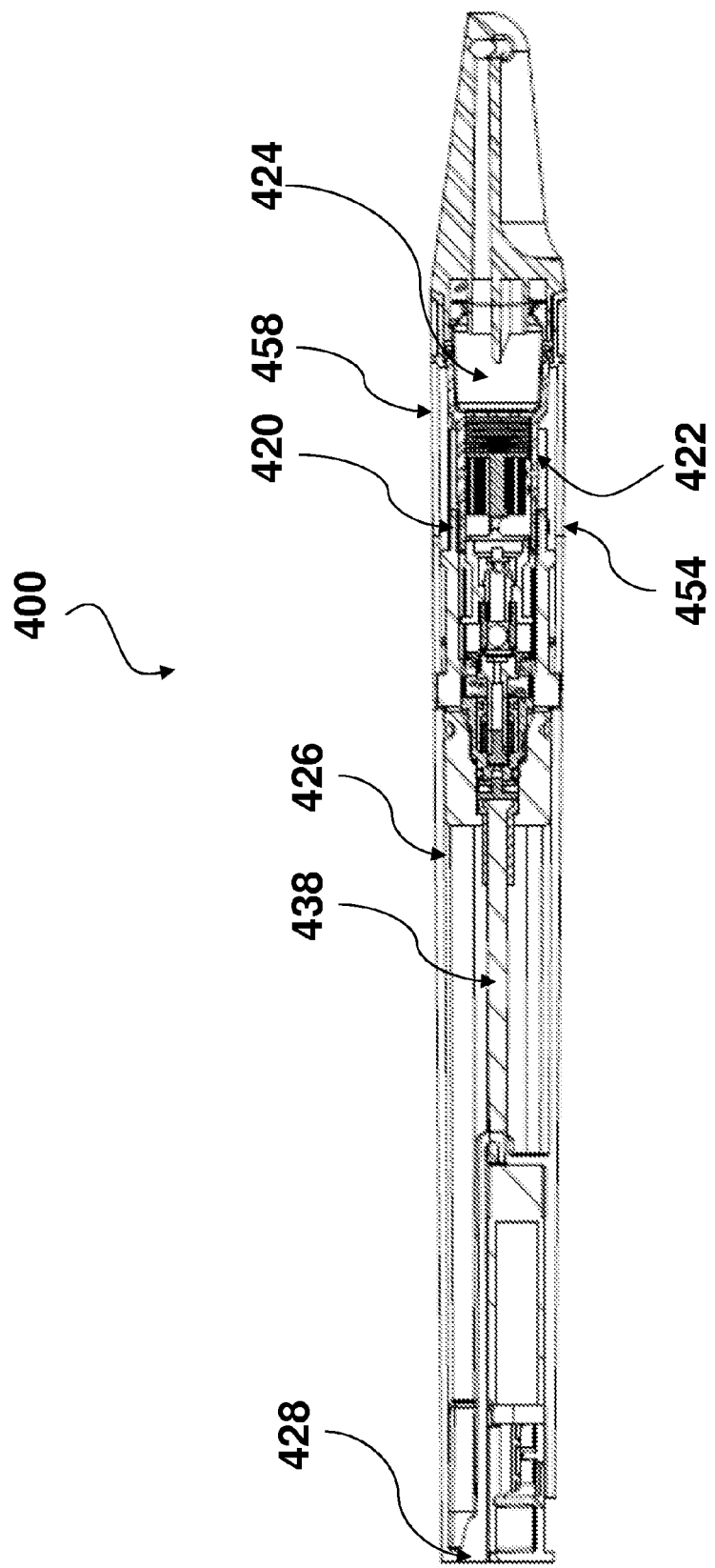
FIG. 4 demonstrates a device wherein fuel is supplied to the tank through a filling valve and compressed liquid fuel can be drawn for use by a wick.

FIG. 4 demonstrates a detailed example of some components of a device 400 of the invention. In FIG. 4, fuel is supplied to the tank 426 through a filling valve 428 and compressed liquid fuel can be drawn for use by a wick 438. In the example in FIG. 5, the flow of gaseous fuel is then limited by a compressed foam flow restrictor 540 and may only leave through a valve orifice 542. There is a single elastomeric stopper 544 which prohibits the movement of gas. The use of a single stopper 544 for all gas flow regulation can increase the simplicity and reliability of the system significantly. The stopper 544 is also referred to herein as a variable flow valve 544. Also included can be a simple but separate means for regulating butane flow with temperature, dispensing an extremely low flow of gas to keep a portion of catalyst above its light-off temperature, and allowing the user to turn on and off the device 500. The variable flow valve 544 can allow all three of these needs to be handled by a single valve.

The stopper 544 can be connected to a rigid jetting assembly terminating with an electrically insulating component 546. The jet assembly is normally held in a position that allows gas to exit the valve orifice 542 and to enter the jet assembly by a relatively low spring constant biasing spring 548. Gas is limited to only entering the jet assembly by a sliding seal 550. Alternately, a flexible diaphragm could be used. The user is able to defeat this normal flow of gas by sliding an activating slider so that the jetting assembly is held down such that the stopper 544 seals the valve orifice 542; this is the OFF state of the device 500. When the user allows the normal gas flow state by sliding an activating slider to the ON position a piezo-igniter is depressed so that a spark is generated between the jet rosette 552 and the oven heater 522, thereby igniting the flowing gas. As the oven heater 522 begins to reach its operating temperature a series of alternately stacked bimetal discs 532 change shape (transitioning from flat to domed) and act on a pushrod component 534 which in turn presses the jet assembly so that the stopper 544 limits or ceases the flow of gas.

Figure 5:
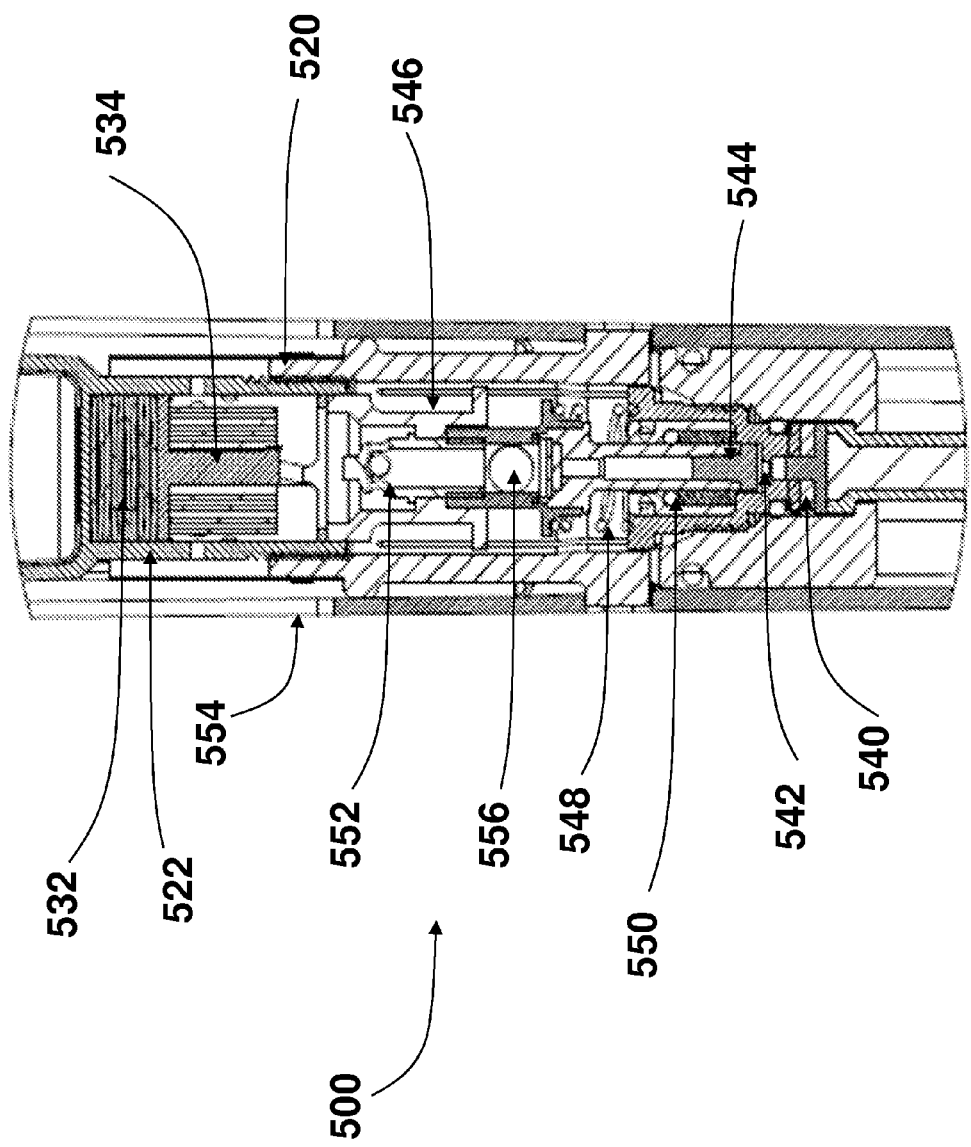
FIG. 5 illustrates a device of the invention comprising a single elastomeric stopper which prohibits the movement of gas and wherein the flow of gaseous fuel is limited by a compressed foam flow restrictor and may only leave through a valve orifice.

By using a bimetallic disc design, a device of the invention may be tuned to a specified temperature regulating range by simply changing the distance between the backstop of the discs and the valve seat. In FIGS. 4-5, by threading the oven heater component 422, 522 into the plastic body 420, 520 of the device 400, 500, the operating temperature can be changed by simply twisting the oven component 422, 522 externally using a tool that mates with the oven. The oven 424 can also be designed to be moved manually by a user. Features can also be incorporated onto the oven 424 for twisting the component.

In FIG. 5, the pushrod component 534 can serve multiple functions. The pushrod 534 can act to transfer longitudinal motion of the bimetallic discs 532 to the jet assembly, which in turn transfers that motion to the valve stopper 544. The pushrod 534 can also hold the catalyst in an easily assembled manner, such as the catalyst being simply wound around the pushrod 534. The pushrod 534 designates a fixed space between the jet rosette 552 and the catalyst, so that initial combustion can easily occur. In an example, the pushrod 534 has roughly the shape of a dumbbell, with two flat, circular surfaces at opposing ends which are used to contact the bimetallic discs 532 at the top, and the insulating component 546 at the bottom. The lower end of the pushrod 534 has large cutouts which allow for gas flow to pass through and initial combustion to take place.

Many devices of the invention use a temperature regulation scheme in that the temperature regulator (bimetallic discs) are located in close proximity to the area where temperature is most critical (at the oven). Related art has typically located the temperature-sensitive component at the flow valve, which can be easily influenced by the cool temperature of expanding fuel gas and has minimally intimate contact with the vaporizing chamber. Examples of related devices and methods are described in U.S. patent application Ser. No. 11/485,168, U.S. Pat. No. 4,819,665, U.S. Pat. No. 4,793,365, U.S. Pat. No. 5,027,836 and PCT Application WO 2006/082571. The regulation scheme of a device of the invention may be tuned to a specific temperature by a simple twist of the oven.

In the exemplary devices of FIGS. 4-5, air enters the jet assembly through inlet apertures 454, 554 and mixes with the butane flow path at the venturi 556. Exhaust gas exits through outlet ports 458.

The user is prevented from touching the hot internal elements by surrounding insulating features. A device of the invention can include insulation for keeping the user from contacting the necessarily hot portion of the device. While greater thermal insulating ability is preferable so that the device performs with the best efficiency possible, an important aspect for the user is to perceive a relatively cool surface temperature. Various strategies can be employed to address the perception of the user regarding the temperature of the device. The device may be wrapped in a thermal insulating material that has enough durability for external use. Materials for this purpose have low thermal conductivity and low thermal capacity (specific heat). The combination of these properties can allow little heat to be transferred to the fingers of the user. Examples of materials with low thermal conductivity and capacity include some polymers and ceramics. A separate strategy is to use standoff features that keep the user from touching the higher temperature area directly. This can also minimize the contact area of the user's fingers and the device to additionally reduce perceived heat. The thermal conductivity and specific heat of the standoff features should be as low as possible.

A heater of a device of the invention can comprise a conductive shell and a catalyst, wherein the shell may be of one or more material formed by welding or pressing together. The catalyst within the heater can be chosen to provide an efficient flameless combustion of the fuel. In some cases, in order to provide a visual chic to the user, the catalyst or heater can emit a color, such as red, when the heater is heating to indicate that the device is activated.

Figure 6:
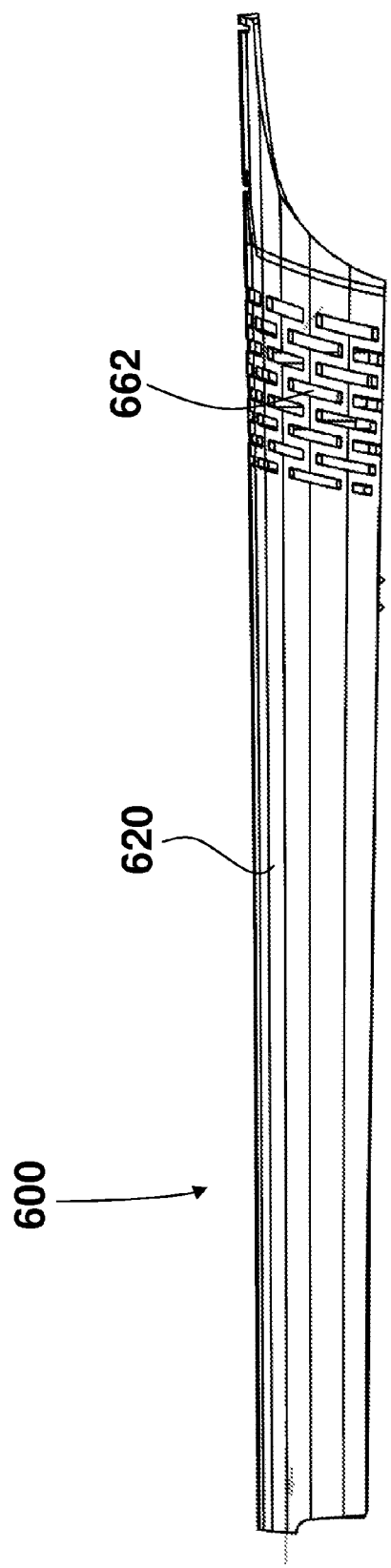
FIG. 6 demonstrates a device in which the plastic body exhaust apertures are located above the heater exhaust apertures and the escaping gas must pass along the heater body and exchange even more of its heat, thereby improving efficiency of the device.

In some cases, the heater can exhaust directly to the surrounding atmosphere through a side aperture. However, as demonstrated in FIG. 1 a device 100 of the invention preferably incorporates a series of smaller apertures 158 around the heater assembly 122 which better transfer heat from the catalyzed gas to the oven 124. Also, as shown in FIG. 6, since the plastic body 620 exhaust apertures 662 are located above the heater exhaust apertures the escaping gas must pass along the heater body and exchange even more of its heat, improving efficiency of the device 600. The use of two barriers (heater wall and body wall), in conjunction with staggering the vent apertures, has the added benefit of improving wind-resistance (for example, ambient wind is less likely to disturb the internal flow of gases, or cool the catalyst to the point that it extinguishes.) The specific geometry of the exhaust path allows for these benefits without inhibiting the initial combustion of gas necessary to initiate catalytic activity. The gas flows smoothly through a continually expanding exhaust area, without torturous turns that could cause the initial burst of gas to extinguish itself.

In the field of combustion catalysts, the light-off temperature is often used to describe the minimum temperature at which the catalyst must be maintained in order to catalyze the exothermic reaction of fuel and oxidant. Only a portion of the catalyst must remain at this temperature to prevent the reaction from extinguishing altogether. The targeted operating temperature of a heater of a device of the invention is close to the light-off temperature of most catalysts, and can make maintaining the catalyst difficult to achieve. The target operating of temperature of the heater can be 180° C. Examples of types of catalysts used in a device of the invention include, but are not limited to, platinum, palladium, and rhodium. The catalyst light-off temperature of a catalyst for use with the invention may be from about 100 to 200° C.

To address the fine difference in temperature of the heater as compared to the light-off temperature a small trickle of gas can flow over the catalyst and/or the catalyst can be shielded from external factors, such as wind. A device of the invention can include a protected exhaust path, meaning that exhaust does not directly exit to the outside air but instead travels along a convoluted path so that the catalyst is difficult to extinguish by wind.

A concern for the reliability of the device of the invention is to maintain catalyst operation at the low target temperatures of the device. A discrete on/off valve alone can have difficulty in this regard because the cycle time between butane bursts can sometimes allow the catalyst to cool to too low of a temperature, and a rapid burst of expanding butane can actually serve to extinguish the catalyst since the butane temperature will be cool. A simple solution that can be incorporated into a device of the invention is to slightly roughen the valve seat surface, or to use a textured stopper surface so that the device can achieve a low-flow of butane just before it closes the flow completely during regulation. This is similar in operation to a needle valve, but much cheaper and easier to implement. A needle valve can also be used in a device of the invention to regulate fuel flow. Some prior art uses a thermal mass so that the light-off temperature can be maintained between regulation intervals. When gas flow resumes between regulation intervals only the area in contact with the thermal mass will initially catalyze the gas, exhausting a reasonable amount of unused fuel. A device of the invention does not require such a thermal mass since the valve seat can act as an analog valve and allow the device to dampen regulation intervals and intensity. A device of the invention can trickle an amount of butane needed to keep the catalyst above light-off temperature, in other words, not overwhelming the catalyst.

As demonstrated in FIG. 3, a device 300 of the invention can be used aerosolize a material contained within a cartridge 370 that can be inserted into the oven chamber 324 of the device 300. With the spark of an igniter (immediately following the start of gas flow), the gas ignites and heat starts conducting throughout the heater assembly 322. Heat transfers to the cartridge 370 by conduction, convection, and/or radiation. The cartridge 370 can be shaped to fill the chamber 324 so as to maximize surface contact for thermal conduction. As the cartridge 370 heats, vapor generates within the cartridge 370 and in the space immediately above it. When a user draws on the device 300, fresh air enters through an air inlet, mixes with the vapor, and the mixture is delivered to the user via the inhalation passage. The air inlet or inlets can be directed downward, so as to improve the extraction of vapor from the cartridge 370. The air inlet can also be directed along a diagonal through the mouthpiece 310, or laterally through the case itself, above the cartridge 370. The air inlet or inlets can have a diameter and direction sized to admit ambient air into the chamber 324 to stir up vapor while not affecting the operating temperature. The air inlet apertures can also regulate the velocity of ambient air entering and mixing with the vapor generated in the oven chamber 424 at either a set rate or a rate chosen by the user. For example, the rate of air entering the device 300 can provide a perception to the user as if the smoke is drawn through a cigarette. Once the cartridge 370 is used, the device 300 can be turned off and the cartridge 370 is removed by opening the oven chamber 324 of the device 300. The cartridge 370 can be removed by hand or by a mechanism that can quickly and easily remove the cartridge 370. This mechanism can include the use of a pin or slide part to eject the cartridge 370 as another part of the device 300 is moved or removed. The removal mechanism could also involve introduction of a foreign object.

A device as shown in FIG. 7 can incorporate a mouthpiece 710 that is connected to the body 720 of the device 700. The mouthpiece 710 can be a hinged component. The mouthpiece 710 can also be manufactured such that it securely fits into place when it is closed onto the device body 720. The device 700 can be intended for use with a cartridge 770 of the invention as is described herein. A cartridge 770 can be inserted into the oven chamber 724 of a device 700 of the invention. As demonstrated in FIG. 7, the mouthpiece 710 can be removed, or hinged open, to provide access to the oven chamber 724 and wherein a cartridge 770 containing a material to be aerosolized can be inserted. The mouthpiece 710 of the device 700 can also be removable or removable and configured for one time use. In this way, multiple users could use the same device 700 but have interchangeable mouthpieces 710. Or if a mouthpiece 710 was soiled, another mouthpiece 710 could easily replace it to prevent having to dispose of the entire device 700. When the device 700 incorporates a mouthpiece 710 that is connected to the body of the device, such as a hinged mouthpiece 710, the device 700 can be operated by a single hand of a user.

A mouthpiece can be made of a high-temperature and food-safe material such as ceramic, glass, or various high-temperature plastics such as polyimide thermoplastic resins, polyetherimide (PEI) resin (brand name Ultem®). Design is simplified by use of high temperature materials, but standard plastics or wood, could also be used with the addition of an insulating component that prevents excessive heat from reaching the user, e.g., the user's lips. Additionally, a mouthpiece can be extended in length, such that the temperature at the mouth of the user is substantially lower than the end of the mouthpiece close to the source of heat.

Figure 7:
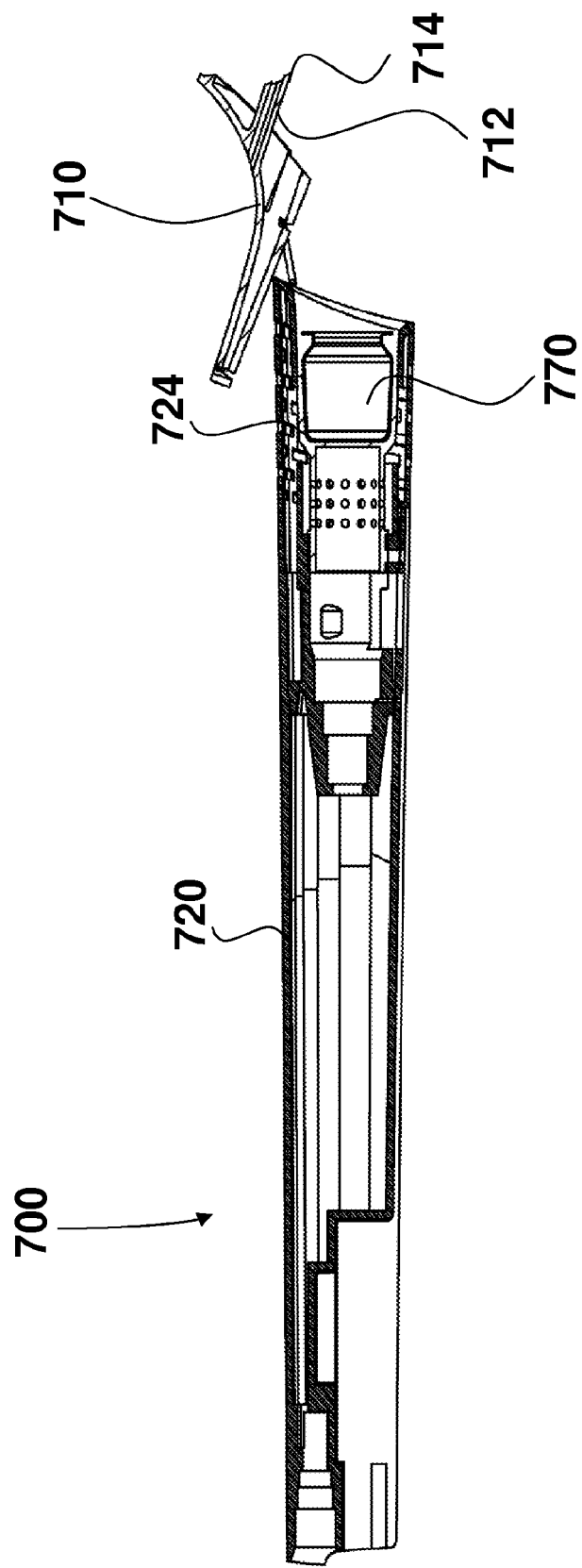
FIG. 7 illustrates a device of the invention with a hinged mouthpiece.

The mouthpiece 710 of a device 700 of the invention, such as the example in FIG. 7 can include a puncturer 712 for piercing a sealed cartridge containing a material for use with the device 700. For example, a hinged mouthpiece 710 can be opened, a cartridge 770 inserted into the device 700, and the mouthpiece 710 can then be closed, which punctures the cartridge 770 for use with the device 710. The puncturer 712 can be any object as would be obvious to one skilled in the art. Preferably the puncturer 712 is a small protuberance 712 that is molded into a mouthpiece 710 and which terminates in a point or edge 714 for puncturing the cartridge 770 when a small amount of force is applied.

Figure 8B:
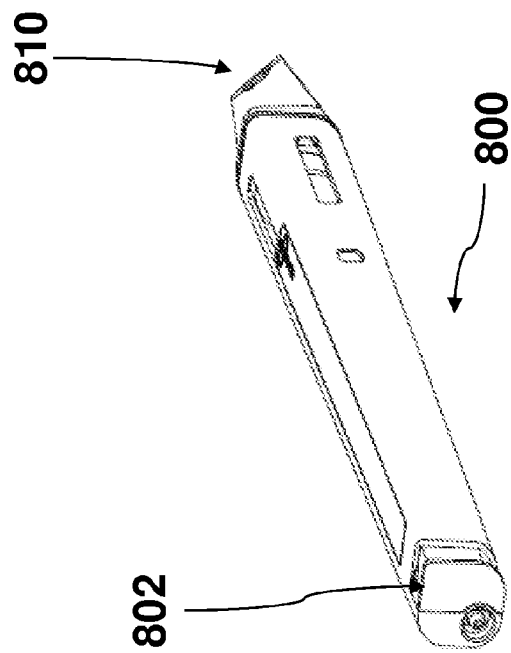
FIG. 8B illustrates the device of FIG. 8A from a different perspective.
Figure 8A:
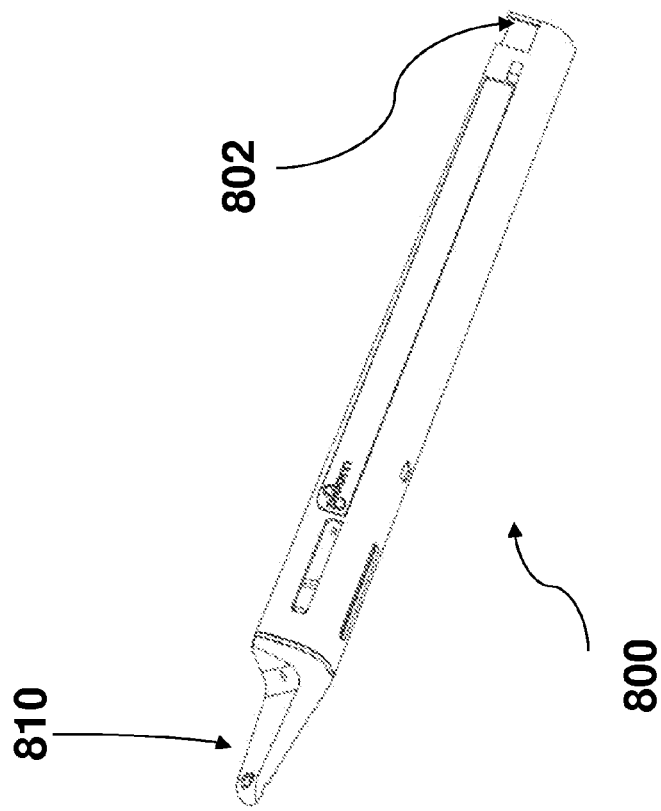
FIG. 8A demonstrates a device wherein the user can slide a strip of material towards the mouthpiece end of the device to turn it on, and then slide the strip back towards the fill port to turn it off.

Some related art devices require two hands for ignition, leading to a clumsy user experience. Preferably a method of ignition using a device of the invention allows for single-handed ignition. As shown in FIGS. 8A-8B, the user can press a button 802 on the device 800 to turn it on, and then press the button 802 again to turn it off. In other embodiments, the user can slide a strip of material towards the mouthpiece end 810 of the device 800 to turn it on, and then slide the strip back towards the fill port to turn it off. Other components can be incorporated into a device of the invention as would be obvious to one skilled in the art, such as a switch. A mechanical advantage may be provided to the user in order to activate an igniter without undue force from the user. Examples of a mechanical advantage include, but are not limited to, levers, four-bar linkages, and other devices as would be obvious to those skilled in the art.

A device of the invention may also provide additional user friendly advantages. For example, the bimetallic object temperature regulator allows for the device to be of a slim, compact, and thus appealing form. Thermal insulating methods prohibit the user from being startled by high heat. A simple on/off mechanism allows for the user to begin and end the use session using a single hand.

II. Cartridge

Figure 9:
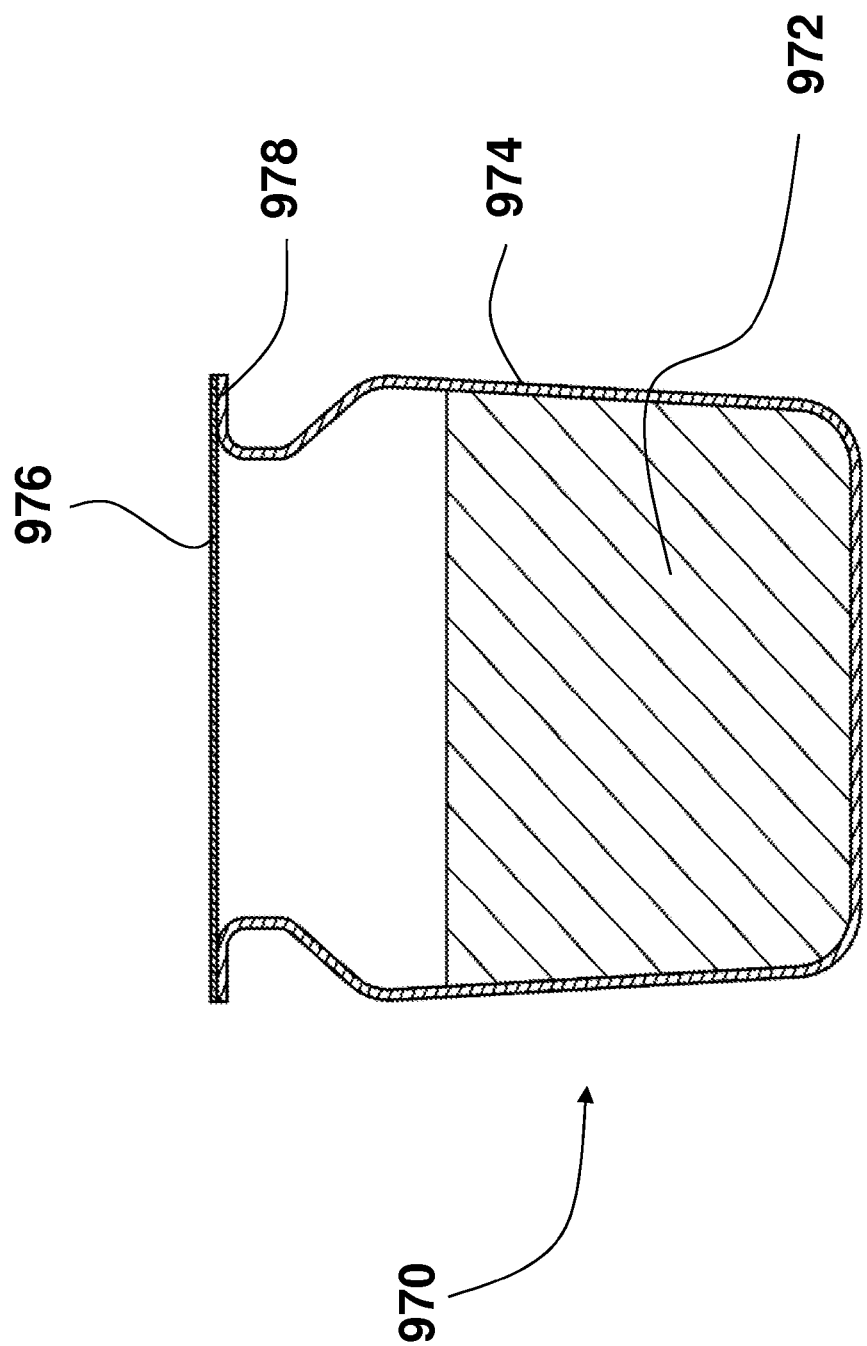
FIG. 9 illustrates a cartridge that can contains a moist vaporizable product for use with a device capable of vaporizing the product comprising a shell, a lid, and a flange for adhering the lid to the shell.

FIG. 9 demonstrates a cartridge 970 that can contains a moist vaporizable product 972 (also referred to sometimes herein as a viscous vaporizable material, a fluidic vaporizable material, a moist smokable material, a fluidic smokable material, or moist vaporizable content) for use with a device capable of vaporizing the product 970. In the figure, the cartridge 970 contains a shell 974 that is sealed with a lid 976. In this example, the shell 974 comprises a flange 978 for adhering the lid 976 to the shell 974. The shell 974 of the cartridge 970 or the entire cartridge 970 can be made from a variety of materials including, but not limited to, metals, rigid plastics, flexible plastics, paper, paperboard, cardboard, and wax paper. The shell 974 of the cartridge 970 typically comprises a food-safe material, as in most cases, the cartridge 970 is to be used with a device for inhalation of a substance by a subject. Examples of some food-safe materials include aluminum, stainless steel, polyethylene terephthalate (PET), amorphous polyethylene terephthalate (APET), high density polyethylene (HDPE), polyvinyl chloride (PVC), low density polyethylene (LDPE), polypropylene, polystyrene, polycarbonate, and many varieties of paper products. In some cases, especially when the material is paper, the shell 974 can be lined with a material or a food-safe material to prevent both drying of the moist vaporizable content 972 and to protect the moist vaporizable content 72.

Preferably a cartridge formed and shaped for easier insertion into an oven chamber of a device of the invention and to snugly fit into the cavity of the oven chamber for improved thermal conduction and vaporization. Cartridges can be formed and wrapped in a process that does not produce significant amount of harmful gases.

A shell of a cartridge can be lidded with, for example a heat-sealable lidding film, to make a fully enclosed and airtight cartridge. A sealed cartridge of the invention can have the advantage of preserving freshness of the contents, and preventing spill of the materials within the cartridge during shipment or handling by the user.

The lid of a cartridge can also be made by a variety of materials. Typically, the lid comprises a food-safe material. The lid can be sealed onto the cartridge after the moist vaporizable content is inserted into a cartridge of the invention. Many methods of sealing the lid upon the shell of a cartridge are known to those with skill in the art. One example of a method of sealing the lid on a shell of a cartridge comprising a flange is heat sealing. Preferably, the lid of the cartridge is considered food-safe to at least about 400° F. The lid can be a commercially-available film for use with foods cooked in a conventional oven, and are often referred to as dual-ovenable (for microwave and conventional oven use). The dual-ovenable films typically comprise of a PET (polyethylene terephthalate) base layer and an APET (amorphous polyethylene terephthalate) heat-sealing layer. Such lidding films can readily be metallized, or foilized in advance, preferably with aluminum to improve the barrier performance of the film regarding moisture, oxygen and other gases. Metallized films can be produced by common converting processes known to those skilled in the art.

Figure 10:
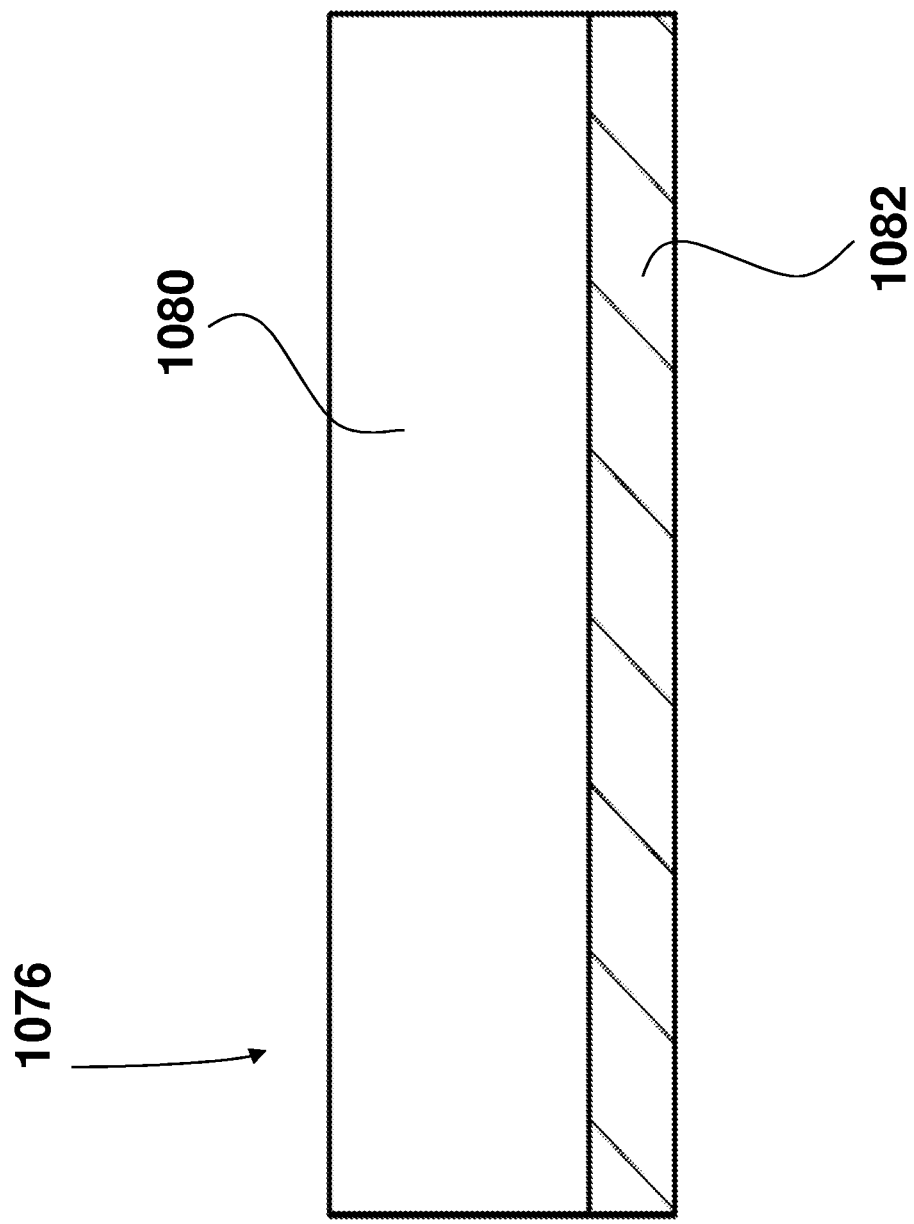
FIG. 10 shows a basic heat-sealable film with PET base layer and APET heat-sealing layer.
Figure 11:
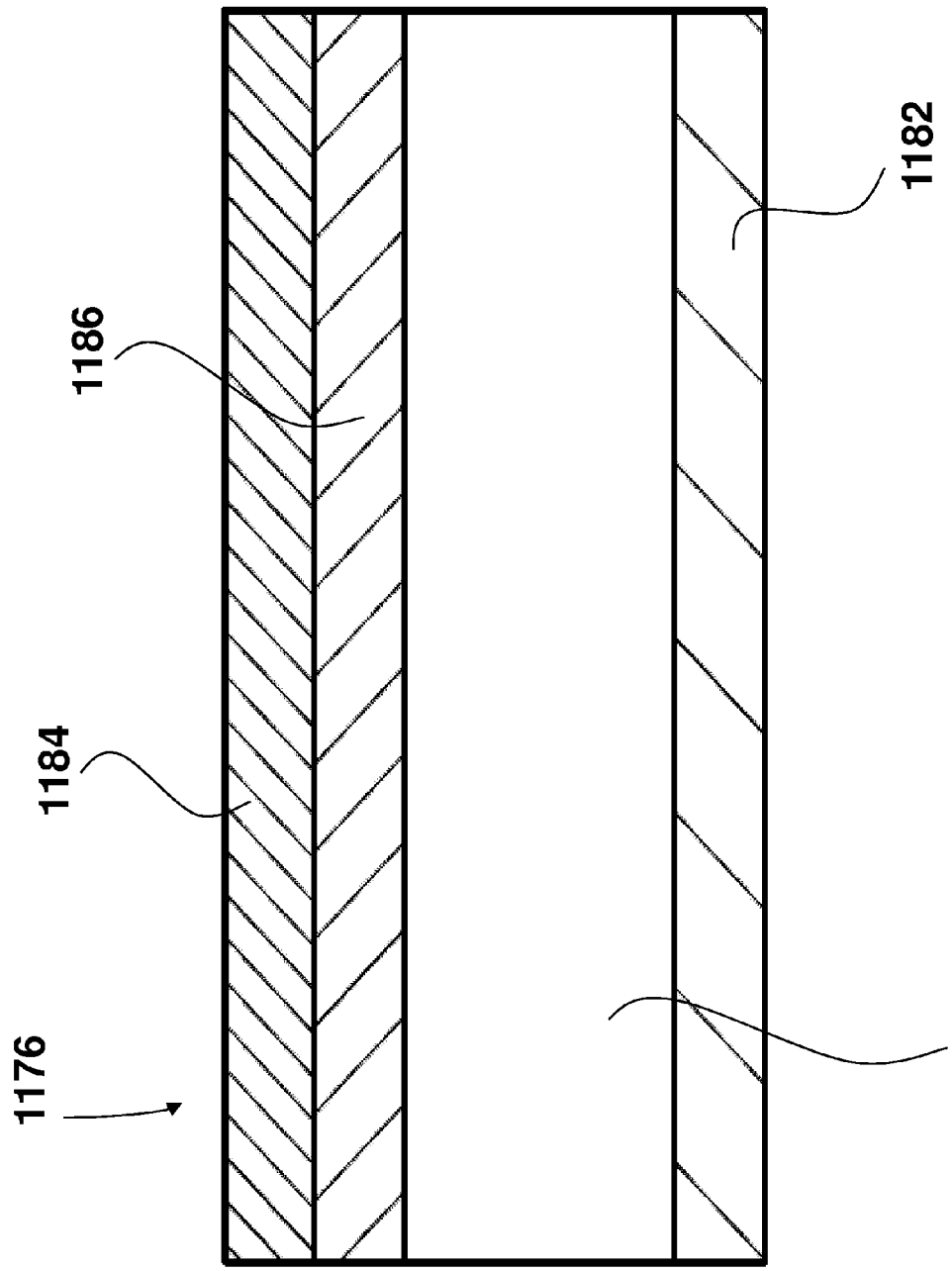
FIG. 11 shows a composite film with a PET base layer and APET heat-sealing layer, but with additional metal layer and metal adhesion layer.

For illustration, FIG. 10 shows a basic heat-sealable film 1076 with PET base layer 1080 and APET heat-sealing layer 1082. FIG. 11 shows a composite film 1176 with a similar PET base layer 1180 and APET heat-sealing layer 1182, but with additional metal layer 1184 and metal adhesion layer 1186. In both cases, the APET heat-sealing layer 1182 is what comes in contact with a flange of a shell of a cartridge of the invention.

The material of a cartridge of the invention and the shell can serve to preserve the freshness of the fill material, and increase shelf life of the cartridges. A metallized cartridge or lid or shell can also improve the visual appeal and perceived value of the cartridges. The material of the cartridge can also allow for improved printing and visibility of product information such as brand and indication of flavor.

Figure 12:
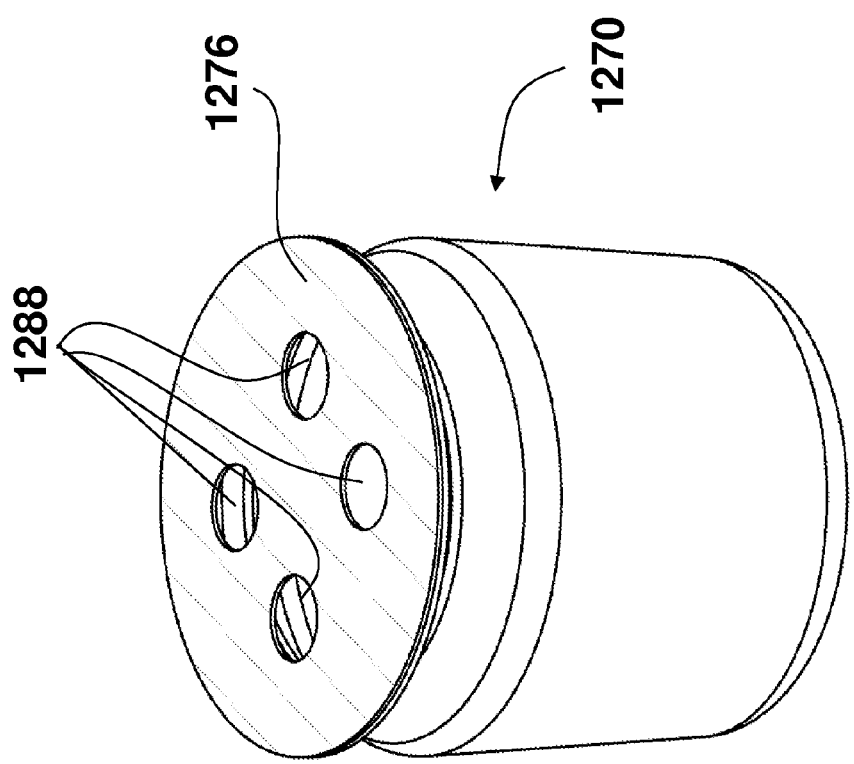
FIG. 12 illustrates a cartridge of the invention containing a moist vaporizable product and comprising apertures or vents to allow the content within the cartridge to have access to the environment.

A cartridge 1270 of the invention that contains a moist vaporizable product can have apertures or vents 1288 in the cartridge 1270, as demonstrated by the example cartridge 1270 in FIG. 12. These apertures 1288 can allow for the content within the cartridge 1270 to have access to the environment. Some types of contents may need or find the access to the environment advantageous.

The exemplary cartridge 1270 in FIG. 12 may also be composed of a material that can be punctured or opened when put into a device capable of vaporizing the contents of the cartridge 1270. For example, if a cartridge 1270 is heated to a certain temperature, the contents vaporize, and the aperture or apertures or openings 1288 created by the device allow the vapor content from the heated cartridge 1270 to escape. In a different manner, the cartridge 1270 may comprise a lid or a seal 1276 that can be opened immediately prior to the cartridge 1270 being inserted within a device.

Figure 13:
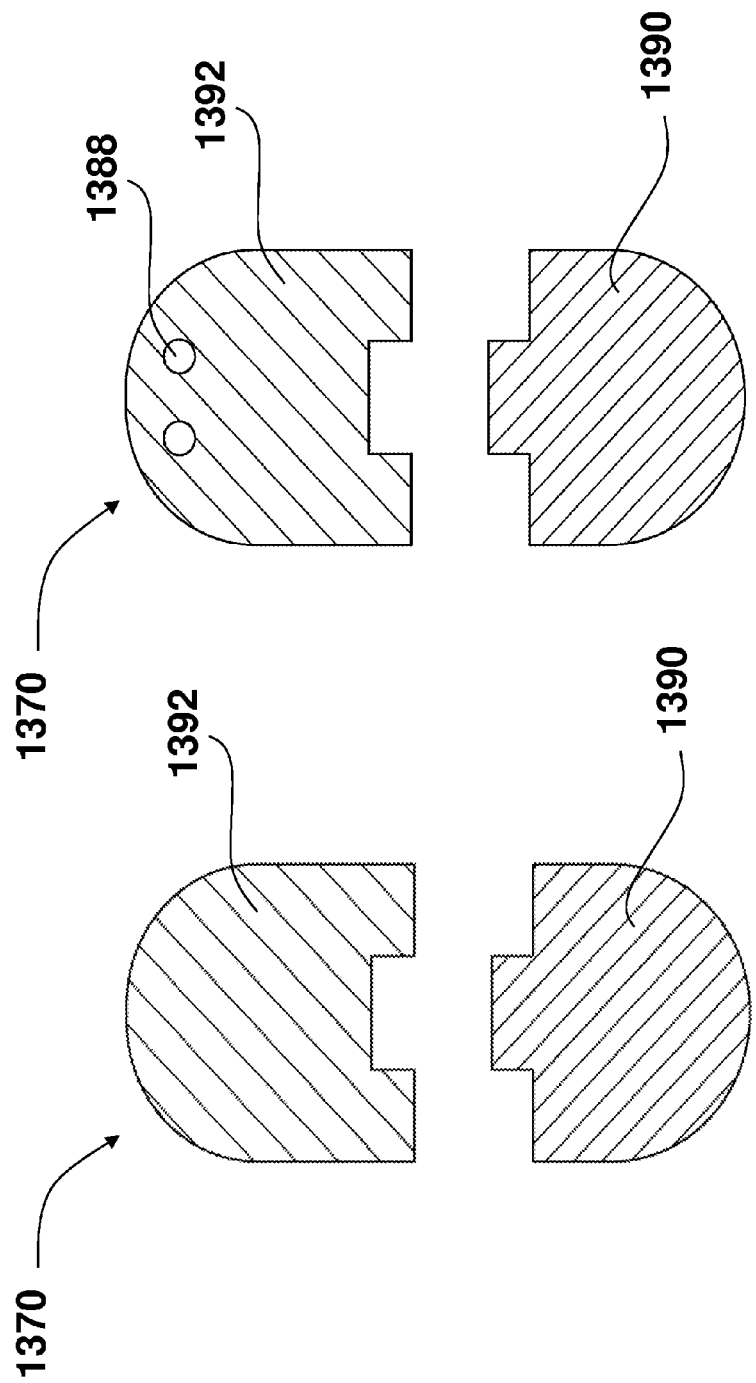
FIGS. 13A-B illustrate cartridges with two portions that can fit together and may have apertures or vents for releasing a vapor from the contents of the cartridges.

The portions of a cartridge can be of FIG. 13A, a cartridge 1370 with two portions 1390, 1392 can be fit together, or have a mechanism for sealing the two portions 1390, 1392 together. FIG. 13B demonstrates a cartridge 1370 that is put together, with each portion containing apertures or vents 1388 for releasing a vapor from the contents of the cartridge 1370 when the cartridge 1370 is heated.

In many cases, a cartridge of the invention is intended for a single use and to be disposable. However, some types of cartridges, such as those that have methods for sealing two portions together, could be used multiple times as a reusable cartridge.

A cartridge can be provided or sold to an end user containing a single use of a moist vaporizable product. The type of product contained within the cartridge can be stamped or written on the cartridge, or indicated by the color, size, or shape of the cartridge. However, a cartridge can be filled by an end used with a moist vaporizable product.

As intended for use by the end consumer, a sealed cartridge of the invention can be inserted into the oven chamber of the device of the invention. The mouthpiece of the device is then returned to the closed position, at which point it can puncture the film on the top of the cartridge. Vapor generated by the heating process is then allowed to exit the cartridge and be inhaled by the user through the mouthpiece.

III. Aerosolized Materials

Any material that is capable of being aerosolized and inhaled by a user may be incorporated into a device or cartridge of the invention as would be obvious to one skilled in the art. It is of particular interest that the material provides an experience to the user either in terms of tactile response in the respiratory tract, or in terms of visual feedback regarding the exhalation of the inhaled material. For example, many materials have be contemplated for use with the present invention including, but not limited to, those containing tobacco, natural or artificial flavorants, coffee grounds or coffee beans, mint, chamomile, lemon, honey, tea leaves, cocoa, and other non-tobacco alternatives based on other botanicals. A device or cartridge of the invention can also be compatible for use with pharmaceutical compounds or synthetic compounds, either for pharmaceutical or pleasurable use. Any such compound which can be vaporized (or volatized) at a relatively low temperature and without harmful degradation products can be suitable for use with a cartridge or device of the invention. Examples of compounds include, but are not limited to, menthol, caffeine, taurine, and nicotine.

Active elements contained in botanicals vaporize at different temperatures. The device can be calibrated to establish a single stable temperature, intended for vaporizing specific products, for example. A controller can also be used to select a variety of temperature settings. The user would choose which setting based on the type of cartridge used. The controller can also affect a desired temperature mechanically, such as by changing flow rate of the valve, or electronically, such as by electromechanical valve and micro-controller intermediary. For example, to change the operating temperature of a device of the invention, the oven chamber can be moved in respect to the temperature regulator, such as bimetallic discs.

Here, tobacco or tobacco material is defined as any combination of natural and synthetic material that can be vaporized for pleasure or medicinal use. In one embodiment of the present invention, a cartridge can be prepared using cured tobacco, glycerin, and flavorings. Those skilled in the art of tobacco product manufacture are familiar with these and other ingredients used for cigarettes, cigars, and the like. The cartridge can be produced by chopping tobacco into fine pieces (for example, less than 2 mm diameter, preferably less than 1 mm), adding the other ingredients, and mixing until even consistency was achieved. In another embodiment, a cartridge can be prepared by processing the fill material into an even paste-like consistency (for example, particle size less than 1 mm), which facilitates the processing of filling the cartridge, for example, by use of an auger filler, peristaltic pump or a piston pump.

Preferably the material for use with a device of the invention or contained within a cartridge of the invention comprises at least one of a vapor-forming medium and a medium for providing a tactile response in a respiratory tract of a user. The aerosolized product from the material inserted into a device can be a combination of vapor phase gases as well as small droplets which have condensed out of vapor phase and remain suspended in the gas/air mixture (the latter constitutes the visible portion of the inhaled substance).

Propylene glycol (PG), glycerin, or a combination of both can be used as vapor-forming medium. Other vapor-forming media can be used with a cartridge and device of the invention. The vapor-forming medium serves to produce a visual vapor, such as a smoke-like vapor, when heated. This vapor can be visualized both before inhalation and during exhalation of the medium. PG has some advantages as compared to glycerin alone, as it exhibits a much higher vapor pressure at equivalent temperature and allows the device to operate at a lower temperature. Reducing the operating temperature conserves energy, and potentially can further improve the health benefits of using this system.

In some cases, vapor resulting from PG that is inhaled by the user can partially absorb in the respiratory tract. If this occurs, it can appear as though the user is expelling primarily air. This differs from the conventional smoking experience in that in the case of smoking, users can typically see and play with expelled smoke as they exhale. Because the visual vapor created by heating glycerin can be seen upon exhale, some preparation of fill material for this invention can comprise a combination of both glycerin and PG. In these embodiments, the PG allows for high densities of visual vapor which the user can see/experience prior to inhaling as well as a tactile response in the respiratory tract, and the addition of glycerin allows for increased amounts of vapor to be seen or otherwise experienced upon exhale.

One method of manufacturing the material for use in a device or cartridge of the invention is to combine cured tobacco leaves with the other ingredients at low heat, and then allow the mixture to incorporate or marinate at room temperature for an extended period of time, from one day to as long as three weeks (depending on the particular recipe and flavors used). The material can then processed by chopping into even consistency with particles 1-2 mm in diameter and inserted into the cartridge, or directly into the device. Alternatively, the material can be processed into a more even, paste-like consistency for improved handling in conventional pump equipment, as described herein.

Example methods of filling a material into a cartridge included an auger fill method and a piston pump method. Both of these are common fill processes used in the packing industry for food and pharmaceutical goods. Either method allows for loading a repeatedly controlled volume of fill material (for example, about 0.25 cubic centimeters) into the shell. The filled shell can then be lidded using the heat-sealable lidding film. The fill and seal operations can be combined on an indexing machine known to those skilled in the art of food and pharmaceutical packaging.

IV. Uses

Figure 14:
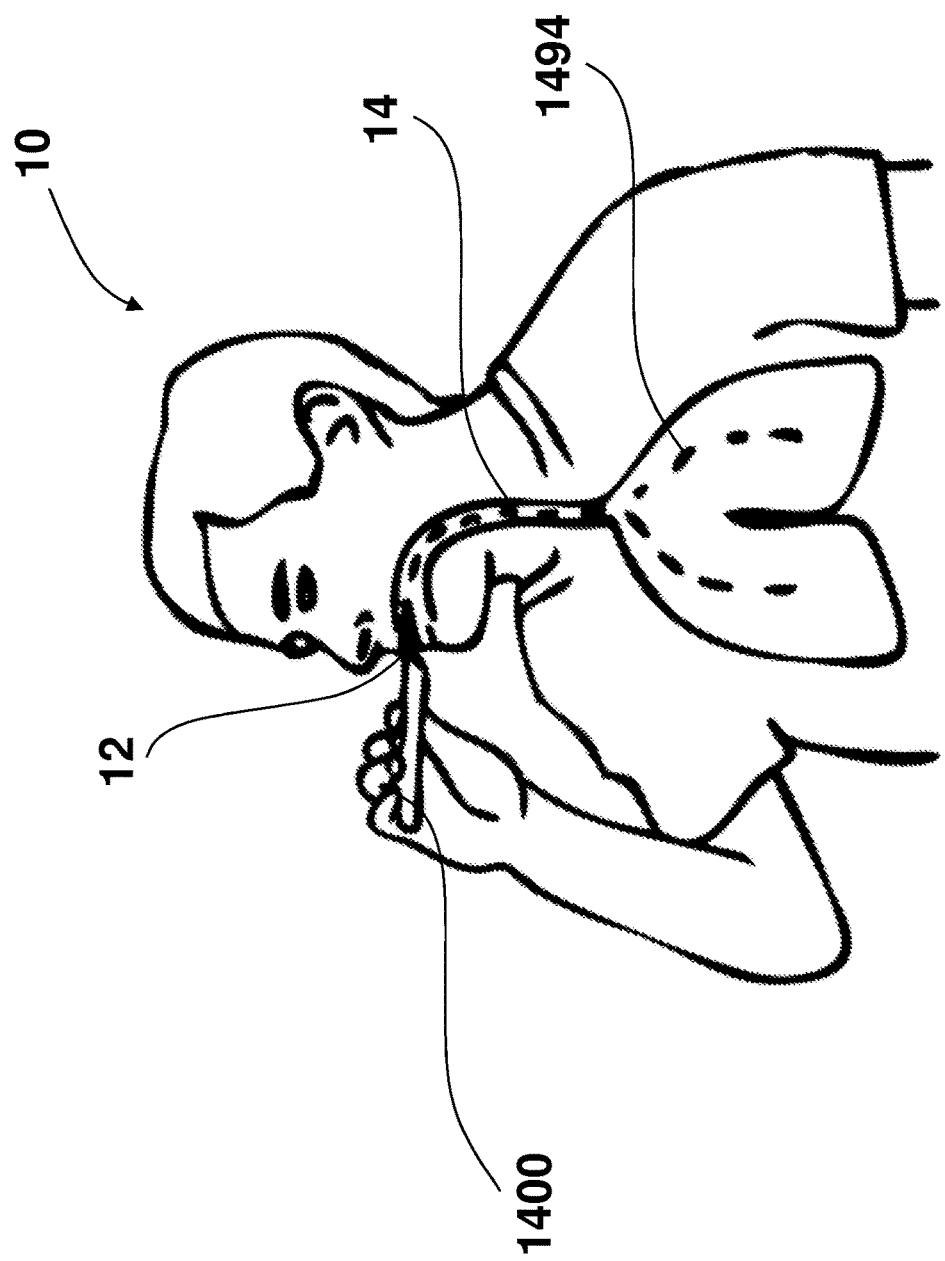
FIG. 14 demonstrates an exemplary method of use of a device of the invention that can emulate smoking by still providing many of the desirable effects of smoking required by a user while reducing Hoffman analyte intake.

The device can emulate smoking by providing many of the desirable effects of smoking required by a user. An example of a method of use of a device and/or cartridge of the invention is demonstrated in FIG. 14. A vapor-forming medium as described herein can be combined with a tobacco material and inserted into a device 1400 of the invention either directly or using a cartridge of the invention. The tobacco material provides to the user the inhalation of substances 1494, such as nicotine, but not many of the tar-type substances, such as many of the Hoffmann analytes (see below), that accompany burning the tobacco material. A device 1400 of the invention can be used in a similar manner to a cigarette or other smoking article by placing the mouthpiece of the device 1400 into contact with the mouth 12 of a user 10. However, without the smoke or the feel of smoke, the user may not be satisfied with the experience. In order to provide a tactile response to the inhalation of the tobacco material, the vapor-forming medium 1494 can be added, such as propylene glycol, that can be absorbed in the respiratory tract 14.

Figure 15:
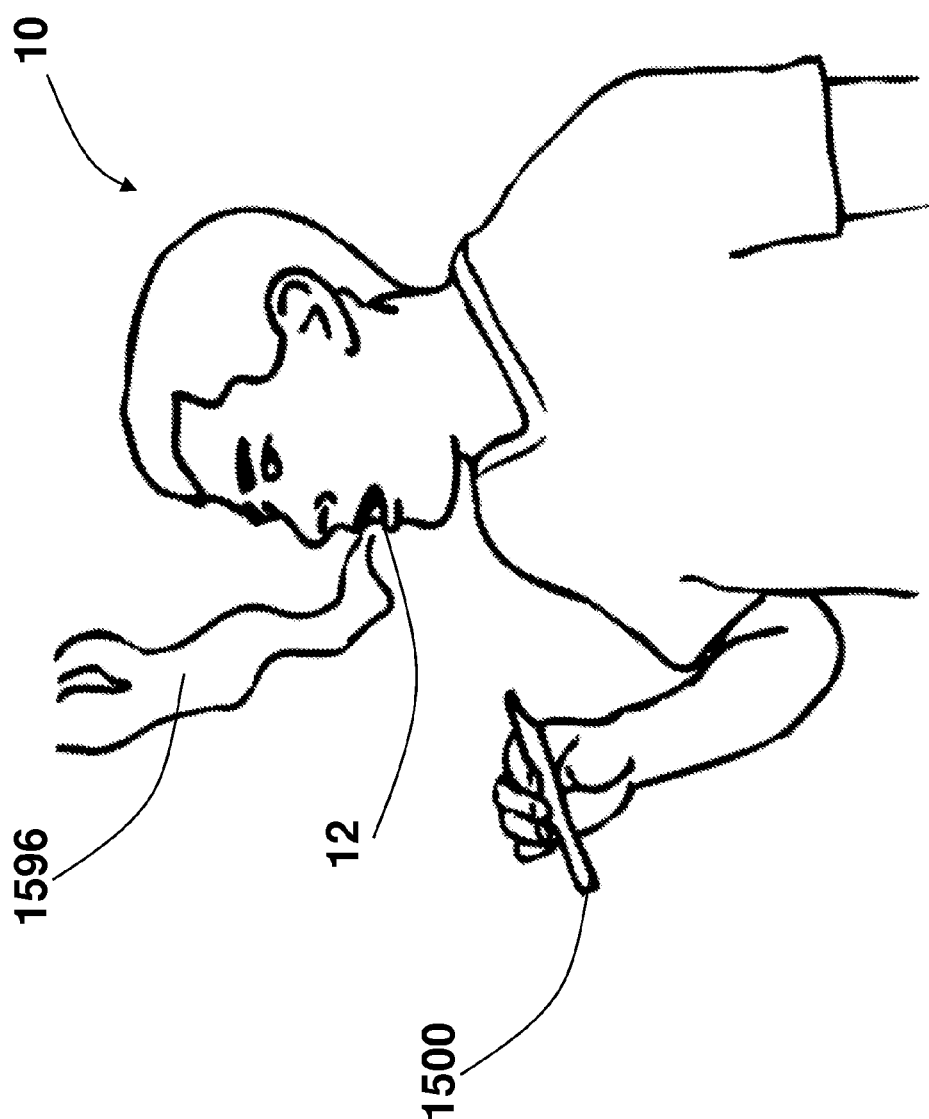
FIG. 15 demonstrates an exemplary method of use of a device of the invention wherein the user has received inhaled tobacco substances from a device of the invention in a manner that has reduced the Hoffman analyte intake of the user by at least 70% and the user may exhale a visible vapor from the vapor-forming medium to provide a similar visual aide to that of exhaled smoke in the act of smoking.

Also, when smoking a tobacco material, the smoke may provide a visual aide and/or visual recognition to the user. In order to provide a similar visual aide, the vapor-forming medium may contain a substance, such as glycerin, that can be visualized before and during inhalation, as well as during exhalation. In an exemplary method of use demonstrated in FIG. 15, the user 10 has received inhaled tobacco substances from a device 1500 of the invention in a manner that has reduced the Hoffman analyte intake of the user 10 by at least 70%. After the intake of the substance, the user may exhale a visible vapor 1596 from the vapor-forming medium through the mouth 12. The visible vapor 1596 can provide a similar visual aide to that of exhaled smoke in the act of smoking.

V. Hoffman Analytes

Cigarette smoke is a complex mixture of thousands of chemical constituents. Many of these have been linked to smoking-related illnesses. A standard reference on the more harmful compounds found in cigarette smoke is the Hoffmann analytes list recognizing about 44 different analytes that may be present in mainstream smoke. It is named in honor of Dietrich Hoffmann, a biochemist and leading authority on tobacco carcinogenesis. This list contains chemicals commonly associated with the health risks of smoking. These analytes and chemicals include, for instance, ammonia, aminonaphthalenes, benzopyrene, formaldehyde, acetaldehyde, acetone, methyl ethyl ketone, butyraldehyde, hydrogen cyanide, nitrous oxides, tobacco-specific nitrosamines (TSNAs), pyridine, quinoline, hydroquinone, phenol, cresols, tar, nicotine, carbon monoxide, 1,3-butadiene, isoprene, acrylonitrile, benzene, toluene, styrene, and various others. It has been determined that some Hoffmann analytes may be unwanted in the mainstream smoke from a smoking article. As such, extensive research has been conducted on reducing Hoffmann analytes. The Hoffmann analytes may also be carcinogenic and a device for smoking or emulating smoking would be desirable.

Using a device of the invention, a tobacco material can be aerosolized without burning the material. By aerosolizing the tobacco, many of the unwanted chemicals and Hoffmann analytes are not inhaled by the user. For example, a device of the invention can reduce the inhalation of Hoffmann analytes by about 70% or more. In some embodiments, a device of the invention can reduce the inhalation of Hoffmann analytes by about 50% or more. In some embodiments, a device of the invention can reduce the inhalation of Hoffmann analytes by about 60% or more. In some embodiments, a device of the invention can reduce the inhalation of Hoffmann analytes by about 70% or more. In some embodiments, a device of the invention can reduce the inhalation of Hoffmann analytes by about 80% or more. In some embodiments, a device of the invention can reduce the inhalation of Hoffmann analytes by about 90% or more.

VI. Ames Assay

The bacterial reverse mutation test was originally developed by Ames et al. The Ames assay serves as a predictor for compounds that might cause carcinogenesis in humans. The method has been widely adopted, and the FDA incorporates it as part of a more comprehensive study of toxicity for new food additives and drugs. The same test has been widely used to study the toxicity of tobacco products and tobacco smoke. The Ames test is a biological assay to assess the mutagenic potential of chemical compounds. As cancer is often linked to DNA damage, the test also serves as a quick assay to estimate the carcinogenic potential of a compound. In comparison, the standard tests for carcinogenicity done on rodents take years to complete and are expensive. The Ames test uses several strains of the bacterium *Salmonella typhimurium* that carry mutations in genes involved in histidine synthesis, so that they require histidine for growth. The variable being tested is the mutagen's ability to cause a reversion to growth on a histidine-free medium. The tester strains are specially constructed to have both frameshift and point mutations in the genes required to synthesize histidine, which allows for the detection of mutagens acting via different mechanisms. Some compounds are quite specific, causing reversions in just one or two strains. The tester strains also carry mutations in the genes responsible for lipopolysaccharide synthesis, making the cell wall of the bacteria more permeable, and in the excision repair system to make the test more sensitive. Rat liver extract is added to simulate the effect of metabolism, as some compounds, like benzopyrene, are not mutagenic themselves but their metabolic products are. In order to perform an assay, the bacteria are spread on an agar plate with a small amount of histidine. This small amount of histidine in the growth medium allows the bacteria to grow for an initial time and have the opportunity to mutate. When the histidine is depleted, only bacteria that have mutated to gain the ability to produce histidine will survive. The plate is incubated for 48 hours. The mutagenicity of a substance is proportional to the number of colonies observed.

As demonstrated in Example 2 below, device of the invention for use with a tobacco containing material can show significant improvement in Ames assay results as compared to many types of smoking tobacco. Thus, a device of the invention can provide many of the substances of the tobacco, such as nicotine, to a user while not providing some key carcinogenic components that are associated with the burning or smoke of tobacco.

Example 1

Cigarette smoke is a complex mixture of thousands of chemical constituents. Many of these have been linked to smoking-related illnesses. The Hoffman analytes list is a standard reference on the more harmful compounds found in cigarette smoke. A set of 52 target compounds will be selected based on the Hoffman list. It is expected that the vapor produced by a device of the invention will reduce the levels of these target compounds by a significant amount (70% reduction or greater).

Constituent testing of a prototype device of the invention and a reference cigarette (KY2R4F) will be conducted in a laboratory. Samples from both types of devices will be acquired onsite, in automated smoking machines and under the Canadian Intense regime (55 cubic centimeter (cc) puffs every 30 seconds). It is believed that this method approximates actual smoking conditions better than the FTC regime (35 cc puffs every 60 seconds). Arista has developed extensive protocols for the analysis of the target compounds, based on literature. These protocols will be employed for testing. Methods of collection and extraction for each group of analyte are summarized in TABLE 1.

TABLE 1

Hoffman Analyte Analysis

| Analyte | Collection method | Extraction Method | Analysis Method |
|---|---|---|---|
| Ammonia | Five cigarettes through a 44-mm Cambridge filter pad with two impingers containing 20 ml of 0.01N MSA. | The pad is extracted with the impinger solutions. | Ion chromatography (IC) with a Dionex IonPac CS14 cation exchange analytical column. |
| Aromatic Amines 2-Aminonaphthalene 3-Aminobiphenyl 4-Aminobiphenyl (3 total) | Five cigarettes through a 44-mm Cambridge filter pad. | Extract pad with 5% HCl and internal standards. Liquid-liquid extraction with dichloromethane. The eluent is collected and then concentrated. Trimethylamine is added and the extract is derivatized with pentafluoropropionic anhydride. The resultant solution is eluted through a florisil column and then concentrated before analysis. | Gas chromatography-mass spectrometry selective ion monitoring (GC/MS SIM) with a J&W DB5MS, 30-m × 0.25-mm × 0.25-μm film thickness. |
| Polynuclear Aromatic Hydrocarbons Benz(a)anthracene Benzo(b)fluoranthene Benzo(j)fluoranthene Benzo(k)fluoranthene Benzo(a)pyrene Chrysene Dibenz(a,h)anthracene Dibenzo(a,i)pyrene Dibenzo(a,l)pyrene Indeno(1,2,3-c,d)pyrene 5-Methylchrysene (11 total) | Five cigarettes through a 44-mm Cambridge filter pad. | Add internal standard and then extract pad with mixture of cyclohexane and benzene. Filter through a silica solid phase extraction (SPE) cartridge and concentrate. Add a mixture of 33% methanol in water and put through a C18 SPE cartridge. Wash with 30% methanol in water and extract with 1.5 mL of benzene for analysis. | GC/MS SIM with a J&W DB5MS, 30-m × 0.25-mm × 0.25-μm film thickness. |
| Carbonyls Formaldehyde Acetaldehyde Acetone Acrolein Propionaldehyde Crotonaldehyde Butyraldehyde Methylethylketone (8 total) | One cigarette through two impingers containing 25 mL of 2,4-dinitrophenylhydrazine and perchloric acid in acetonitrile. | The impinger solutions are combined. An aliquot is removed, pyridine is added to the aliquot and the solution is analyzed. | High-pressure liquid chromatography with UV detector (HPLC-UV) with a reversed phase, C18, 250-mm × 4.6-mm column. |
| Hydrogen Cyanide | Mainstream smoke is collected from one to three cigarettes through a 44-mm Cambridge filter pad followed by one impinger containing 0.1N sodium hydroxide. | The Cambridge filter pad is extracted with 0.1N sodium hydroxide. The impinger solution is shaken by hand. | The gas and particulate phases are analyzed separately by continuous flow analysis. |
| Carbon Monoxide | The gas phase smoke is collected in a gas-sampling bag. | Not Applicable | The concentration of CO is determined using a non-dispersive infrared spectrometer (NDIR spectrometer). |
| Nitric Oxide | Puff-by-puff on-line analysis. | Not Applicable | The gaseous phase smoke is passed through a NO chemiluminescence detector. |
| Mercury | Hg is trapped in impingers containing potassium permanganate. | The samples are microwave digested. | Flow injection, cold vapor atomic absorption spectrometry (cold vapor AA) |

TABLE 1-continued

Hoffman Analyte Analysis

| Analyte | Collection method | Extraction Method | Analysis Method |
| --- | --- | --- | --- |
| Metals<br>Nickel<br>Lead<br>Cadmium<br>Chromium<br>Arsenic<br>Selenium<br>(6 total) | The smoke is trapped in an electrostatic precipitation unit. | The CSC is first extracted using methanol and then the solvent is evaporated before digestion with heat and nitric acid. | Analysis by inductively coupled plasma mass spectrometry (ICP-MS). |
| Nitrosamines<br>NNN<br>NNK<br>NAT<br>NAB<br>(4 total) | Five cigarettes through a 44-mm Cambridge filter pad. | Extraction of filter with 0.1N ammonium acetate. | Liquid chromatography tandem mass spectrometry (LC-MS/MS) with electrospray ionization (ESI) using a 2.0 × 50 mm C18 column. |
| Semi-Volatiles<br>Pyridine<br>3-Vinylpyridine<br>Quinoline<br>(3 total) | Three to five cigarettes through a 44-mm Cambridge filter pad followed by an impinger containing methanol and triethanolamine (TEA). | The filter pad and impinger solution are combined. Internal standards are added with orbital agitation. The resultant solution is decanted and analyzed. | Gas chromatography-mass spectrometry (GC/MS) with a J&W DB-Wax, 30-m × 0.25-mm × 0.25-µm film thickness. |
| Phenols<br>Catechol<br>Phenol<br>Hydroquinone<br>Resorcinol<br>m- & p-Cresol<br>o-Cresol<br>(6 total) | Five cigarettes through a 44-mm Cambridge filter pad. | Extraction using a 1% acetic acid in 30% methanol with agitation for 60 minutes. Filter an aliquot of the extract and then analyze. | HPLC/Fluorescence with a reversed-phase column. |
| Volatiles<br>1,3-Butadiene<br>Isoprene<br>Acrylonitrile<br>Benzene<br>Toluene<br>Styrene<br>(6 total) | Three to five cigarettes through a 44-mm Cambridge filter pad followed by an impinger containing methonal maintained at sub-ambient temperature. | The filter pad and cold impinger solution are combined. Internal standards are added and the solution is vortexed briefly. The resultant solution is decanted and analyzed. | GC/MS with a J&W DB5MS, 60-m × 0.25-mm × 1.0-µm film thickness column. |

For each target compound, five replicate tests will be run, both for a device of the invention and the reference cigarette. The differences in mean yield between the two articles will be determined as a percentage. It is expected that a device of the invention will reduce the level of Hoffman analytes by about 70% or more as compared to the reference cigarette.

Example 2

The bacterial reverse mutation test, or "Ames assay," serves as a predictor for compounds that might cause carcinogenesis in humans. This test has been widely used to study the toxicity of tobacco products and tobacco smoke. The objective of this study described here was to screen the smoke condensate of the present invention for mutagenicity in the TA 98 strain of the bacterium *Salmonella typhimurium* using the Ames assay. Strain TA 98 was chosen because it is among the most sensitive strains of *Salmonella typhimurium*, and can detect a wide variety of mutagens. If a dose-dependent response is detected, the smoke condensate is considered to be mutagenic for that strain.

Testing Facility.

Test article preparation (i.e., "smoking" and extraction), chemical constituent analysis and genotoxicity were conducted at Arista Laboratories, 1941 Reymet Road, Richmond, Va. 23237.

Preparation of Extracts of Test Articles.

Three cartridges were "smoked" per each replicate using a smoking device of the present invention connected to an automated rotary smoking machine (Borgwaldt RM-20 CSR) using the following parameters: 1) puff volume of 55 ml; and 2) puff duration of 30 seconds and an air flow according to ISO standards. Total Particulate Matter (TPM) phase was collected onto a 44 mm Cambridge filter pad and extracted into dimethyl sulfoxide (DMSO) Immediately following extraction, TPM samples were aliquoted into individual amber vials and stored at less than or equal to −70° C. for greater than or equal to 48 h prior to testing by the Ames assay. Once thawed and used for testing, TPM extracts were not reused or refrozen.

Mutagenicity Testing (Ames Assay).

Figure 16:
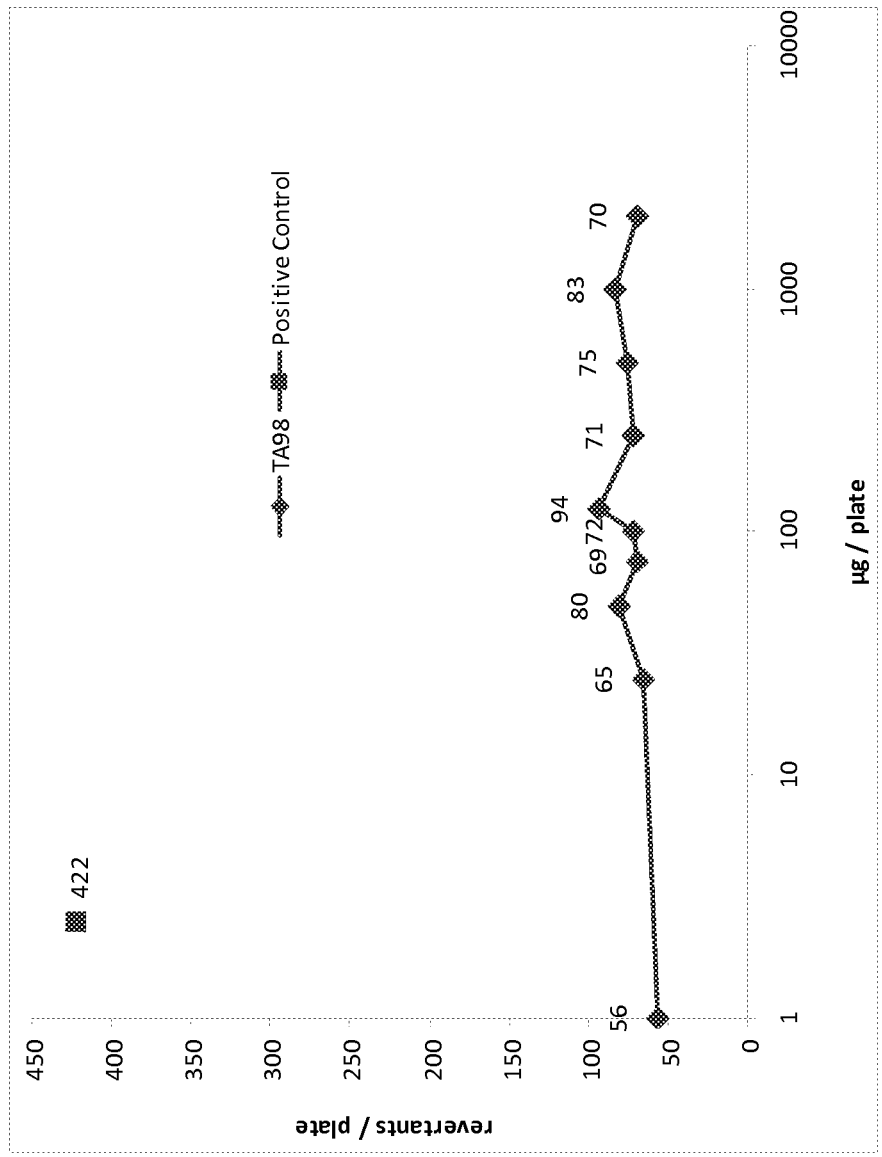
FIG. 16 shows the results of a bacterial mutagenesis test (Ames assay) indicating that particulate generated by smoking the device of the present invention is non-mutagenic.

The Ames assay was conducted on TPM extracts generated during three independent "smoking" sessions. The assay was performed according to according to Arista Standard Operating Procedure #TOX 001. TPM samples were tested in triplicate with the addition of an exogenous metabolic activation system (S9). For each replicate sample, ten concentrations of particulate phase ranging from 0-2000 µg TPM per plate were tested in a minimum of three plates per concentration. Concurrent testing of strain-specific positive controls (with and without S9) and a single concentration (i.e., 100 µg) of the KY2R4F reference cigarette condensate were conducted. The assay was conducted according to Health Canada Official Method 501, second edition, 2004-11-01, Arista Standard Operating Procedure #TOX 001. Results of the Ames assay are shown in FIG. 16. Vehicle and positive controls, KY2R4F and spontaneous revertant concurrently run with each test and pertinent to bacteria strains and incubation conditions were within the expected laboratory control limits or deemed scientifically acceptable by the study director.

Results.

As shown in FIG. 16, the study found no dose-dependent effect of the Total Particulate Matter (TPM) generated by "smoking" the device of the present invention. Moreover, all TPM samples showed a reversion rate less than half that of the control. In contrast, published data for the "1R4F" Kentucky reference cigarette, a cigarette of common tobacco and filter composition, produce a positive-sloping trend for the TA 98 tester strain. See D. W. Bombick et al., "Chemical and Biological Studies of a New Cigarette that Primarily Heats Tobacco. Part 3. In vitro toxicity of whole smoke," Food and Chemical Toxicology, 36:183-190 (1997).

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method of delivering an aerosol to a subject, the method comprising:
    a) deploying an aerosol generating device comprising a heater and a vaporizable material in a vaporization chamber, wherein the vaporizable material comprises a tobacco product and an aerosol-forming medium, wherein the tobacco product comprises fine pieces of tobacco, wherein the fine pieces of tobacco are less than 2 mm in diameter, and wherein the aerosol-forming medium comprises glycerin or propylene glycol;
    b) heating the vaporizable material in the vaporization chamber with the heater of the device to a target temperature, wherein the target temperature is 100° C. to 180° C.;
    c) generating the aerosol in the vaporization chamber, wherein the aerosol contains at least 70% less Hoffman analytes than a common tobacco cigarette; and
    d) delivering the aerosol directly to the subject for inhalation.

2. The method of claim 1, wherein the Hoffman analytes include: ammonia, aminonaphthalenes, benzopyrene, formaldehyde, acetaldehyde, acetone, methylethylketone, butyraldehyde, hydrogen cyanide, nitrous oxides, tobacco-specific nitrosamines (TSNAs), pyridine, quinoline, hydroquinone, phenol, cresols, carbon monoxide, 1,3-butadiene, isoprene, acrylonitrile, benzene, toluene, and styrene.

3. The method of claim 1, wherein the target temperature is 100° C. to 150° C.

4. The method of claim 1, wherein the target temperature is about 150° C.

5. The method of claim 1, wherein the aerosol contains at least about 80% less Hoffman analytes than a common tobacco cigarette.

6. The method of claim 1, wherein the aerosol contains at least about 90% less Hoffman analytes than a common tobacco cigarette.

7. The method of claim 1, wherein the aerosol-forming medium comprises glycerine and propylene glycol.

8. The method of claim 1, wherein the vaporization chamber and heater are within a sealed cartridge, and wherein deploying the aerosol generating device comprises attaching the cartridge to a reusable portion of the device.

9. The method of claim 8, further comprising removing the cartridge from the reusable portion when the vaporizable material is depleted.

10. The method of claim 1, wherein the vaporizable material is a fluidic vaporizable material.

11. The method of claim 1, wherein the tobacco product comprises fine pieces of tobacco, wherein the fine pieces of tobacco are less than 1 mm in diameter.

12. The method of claim 1, wherein the aerosol comprises particles less than about 2 microns in diameter.

13. The method of claim 1, wherein the aerosol-forming medium further comprises a natural or an artificial flavorant.

14. The method of claim 1, comprising a natural flavorant, wherein the natural flavorant comprises lemon flavor.

15. An aerosol generating device comprising:
    a heater; and
    a vaporization chamber comprising a vaporizable material that comprises a tobacco product and an aerosol-forming medium, wherein the tobacco product comprises fine pieces of tobacco, wherein the fine pieces of tobacco are less than 2 mm in diameter, and wherein the aerosol-forming medium comprises glycerine or propylene glycol,
    wherein the device generates an aerosol in the vaporization chamber upon heating the vaporizable material to a target temperature, wherein the target temperature is 100° C. to 180° C.,
    wherein the aerosol in the vaporization chamber is deliverable directly to a user following generation, and
    wherein the aerosol contains at least 70% less Hoffman analytes than a common tobacco cigarette.

16. The device of claim 15, wherein the Hoffman analytes include: ammonia, aminonaphthalenes, benzopyrene, formaldehyde, acetaldehyde, acetone, methylethylketone, butyraldehyde, hydrogen cyanide, nitrous oxides, tobacco-specific nitrosamines (TSNAs), pyridine, quinoline, hydroquinone, phenol, cresols, carbon monoxide, 1,3-butadiene, isoprene, acrylonitrile, benzene, toluene, and styrene.

17. The device of claim 15, wherein the target temperature is 100° C. to 150° C.

18. The device of claim 15, wherein the target temperature is about 150° C.

19. The device of claim 15, wherein the aerosol contains at least about 80% less Hoffman analytes than a common tobacco cigarette.

20. The device of claim 15, wherein the aerosol contains at least about 90% less Hoffman analytes than a common tobacco cigarette.

21. The device of claim 15, wherein the aerosol-forming medium comprises glycerine and propylene glycol.

22. The device of claim 15, wherein the vaporization chamber and heater are within a sealed cartridge.

23. The device of claim 22, wherein the cartridge is configured to be removed from a reusable portion of the device when the vaporizable material is depleted.

24. The method of claim 15, wherein the vaporizable material is a fluidic vaporizable material.

25. A method of delivering an aerosol to a subject, the method comprising:
    a) deploying an aerosol generating device comprising a heater and a vaporizable material in a vaporization chamber, wherein the vaporizable material comprises a tobacco product and an aerosol-forming medium, wherein the tobacco product comprises fine pieces of tobacco, wherein the fine pieces of tobacco are from 1 mm to 2 mm in diameter, and wherein the aerosol-forming medium comprises glycerin or propylene glycol;
b) heating the vaporizable material in the vaporization chamber with the heater of the device to a target temperature, wherein the target temperature is 100° C. to 180° C.;
c) generating the aerosol in the vaporization chamber, wherein the aerosol contains at least 70% less Hoffman analytes than a common tobacco cigarette; and
d) delivering the aerosol directly to the subject for inhalation.

* * * * *